United States Patent [19]
Lociuro et al.

[11] Patent Number: 6,143,739
[45] Date of Patent: *Nov. 7, 2000

[54] BASIC PROLINE-AMIDE DERIVATIVES OF GE 2270 AND GE 2270-LIKE ANTIBIOTICS

[75] Inventors: Sergio Lociuro, Verona; Pierfausto Seneci, Desenzano del Garda; Ermenegildo Restelli, Gerenzano; Romeo Ciabatti, Novate Milanese, all of Italy

[73] Assignee: Biosearch Italia S.p.A., Milan, Italy

[ * ] Notice: This patent is subject to a terminal disclaimer.

[21] Appl. No.: 08/875,707

[22] PCT Filed: Feb. 1, 1996

[86] PCT No.: PCT/EP96/00407

§ 371 Date: Jul. 31, 1997

§ 102(e) Date: Jul. 31, 1997

[87] PCT Pub. No.: WO96/24607

PCT Pub. Date: Aug. 15, 1996

[30] Foreign Application Priority Data

Feb. 7, 1995 [EP] European Pat. Off. ............ 95101597

[51] Int. Cl.[7] .............................. A61K 38/05; C07K 5/06; C07K 7/56
[52] U.S. Cl. .............................. 514/183; 514/9; 530/317; 540/451
[58] Field of Search .................. 514/183, 9; 540/451; 530/317

[56] References Cited

U.S. PATENT DOCUMENTS

| | | | |
|---|---|---|---|
| 5,139,778 | 8/1992 | Selva et al. | 514/9 |
| 5,202,241 | 4/1993 | Selva et al. | 435/71.3 |
| 5,514,649 | 5/1996 | Selva et al. | 514/9 |
| 5,599,791 | 2/1997 | Tavecchia et al. | 540/451 |
| 5,891,869 | 4/1999 | Lociuro et al. | 514/183 |

FOREIGN PATENT DOCUMENTS

| | | |
|---|---|---|
| 451 486 | 10/1991 | European Pat. Off. . |
| 0 494 078 A1 | 7/1992 | European Pat. Off. . |
| 529410 | 3/1993 | European Pat. Off. . |
| WO 92/12172 | 7/1992 | WIPO . |
| WO 96/24607 | 8/1996 | WIPO . |
| WO 97/30078 | 8/1997 | WIPO . |

OTHER PUBLICATIONS

"Novel Antibiotics, Amythiamicins III. Structure Elucidations of Amythiamicins A, B and C" The Journal of Antibiotics, vol. 47, No. 10, pp. 1153–1159, (1994).

*Primary Examiner*—Richard L. Raymond
*Attorney, Agent, or Firm*—Killworth, Gottman, Hagan & Schaeff, LLP

[57] ABSTRACT

The present invention refers to basic amides derivatives of GE 2270 and GE 2270-like antibiotics of general formula (1), wherein the group GE represents the antibiotic core molecule. The amide derivatives of antibiotic GE 2270 of formula (I) are antimicrobial agents mainly active against gram positive bacteria.

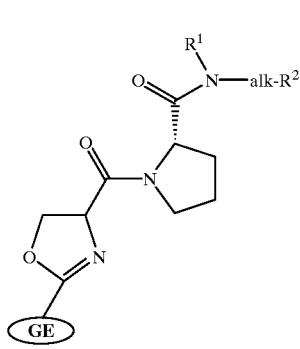

I

43 Claims, No Drawings

BASIC PROLINE-AMIDE DERIVATIVES OF GE 2270 AND GE 2270-LIKE ANTIBIOTICS

The present application is a 371 of PCT/EP96/00407, filed Feb. 1, 1996.

The present invention refers to basic amide derivatives of GE 2270 and GE 2270-like antibiotics of general formula I

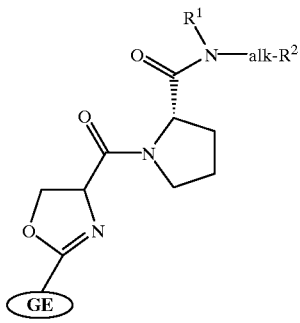

wherein:

$R^1$ represents hydrogen, $(C_1-C_4)$alkyl or di$(C_1-C_4)$alkylamino$(C_1-C_4)$alkylene, alk represents $(C_1-C_4)$alkylene or $(C_2-C_5)$alkylene-carbonyl, $R^2$ represents a $NR^3R^4$ group wherein $R^3$ represents $(C_1-C_4)$alkyl, hydroxy$(C_1-C_4)$alkylene, or di$(C_1-C_4)$alkylamino-$(C_1-C_4)$alkylene, and $R^4$ represents $(C_1-C_4)$alkyl, di$(C_1-C_4)$alkylamino-$(C_1-C_4)$alkylene or hydroxy$(C_1-C_4)$alkylene, or a five or six membered heterocycle ring containing one nitrogen atom and optionally a further heteroatom selected from nitrogen and oxygen, optionally substituted with a group selected from $(C_1-C_4)$alkyl, hydroxy$(C_1-C_4)$alkylene, di$(C_1-C_4)$alkylamino and di$(C_1-C_4)$alkylamino-$(C_1-C_4)$alkylene;

or $R^1$ and alk-$R^2$ together with the adjacent nitrogen atom form a five or six membered heterocycle ring optionally containing a further heteroatom selected from oxygen and nitrogen, optionally substituted with a group selected from $(C_1-C_4)$alkyl, di$(C_1-C_4)$alkylamino, di$(C_1-C_4)$alkylamino$(C_1-C_4)$alkylene, hydroxy$(C_1-C_4)$alkylene and a alk$_2$-$R^5$ group wherein alk$_2$ is $(C_1-C_4)$alkyl and $R^5$ is a $NR^6R^7$ group wherein $R^6$ represents $(C_1-C_4)$alkyl or di$(C_1-C_4)$alkylamino$(C_1-C_4)$alkylene and $R^7$ represents $(C_1-C_4)$alkyl or di$(C_1-C_4)$alkylamino$(C_1-C_4)$alkylene or a five or six membered heterocycle ring containing one or two heteroatoms selected from nitrogen and oxygen, optionally substituted with a group selected from $(C_1-C_4)$alkyl, hydroxy$(C_1-C_4)$alkylene, di$(C_1-C_4)$alkylamino and di$(C_1-C_4)$alkylamino$(C_1-C_4)$alkylene and the group of formula

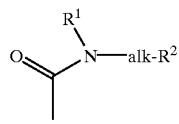

represents the antibiotic core portion of formula

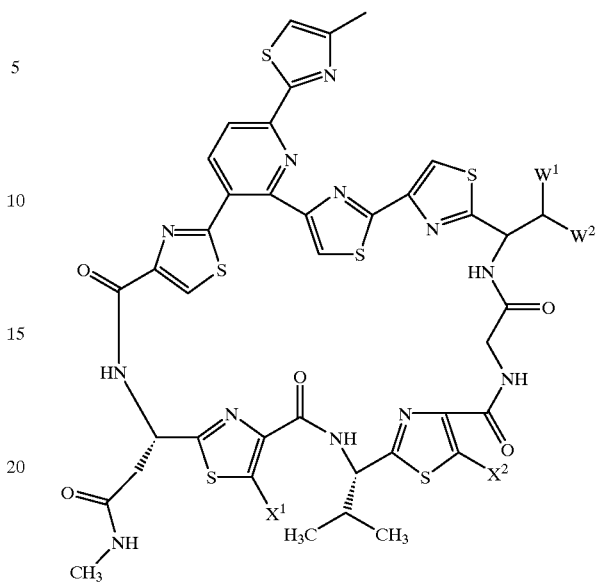

wherein:

$W^1$ represents phenyl $W^2$ represents hydroxy or both $W^1$ and $W^2$ represent methyl, $X^1$ represents hydrogen or methyl, $X^2$ represents hydrogen, methyl or methoxymethylen, with the proviso that when both $W^1$ and $W^2$ are methyl, then $X^1$ is methyl and $X^2$ is hydrogen, or a pharmaceutical acceptable salt thereof.

The present invention refers also to the processes for preparing the compounds of formula I and to the carboxylic acid and protected carboxylic acid derivatives of the above compounds, i.e. the precursors of the compounds of formula I wherein the amidic group:

$$O=\overset{R^1}{\underset{}{\underset{}{N}}}-alk-R^2$$

is substituted by the group —COOY, wherein Y represents hydrogen or $(C_1-C_4)$alkyl.

Antibiotic GE 2270 is prepared by culturing a sample of *Planobispora rosea* ATCC 53773 or a producing variant or mutant thereof and isolating the desired antibiotic substance from the mycelium and/or the fermentation broth. *Planobispora rosea* ATCC 53773 was isolated from a soil sample and deposited on Jun. 14, 1988 with the American Type Culture Collection (ATCC), 12301 Parklawn Drive, Rockville, Md. 20852 Maryland, U.S.A., under the provisions of the Budapest Treaty. The strain has been accorded accession number ATCC 53773.

Antibiotic GE 2270 factor A is the main component of the antibiotic GE 2270 complex. Antibiotic GE 2270 factor A and *Planobispora rosea* ATCC 53773 are described in U.S. Pat. No. 5,139,778.

At present, a number of minor factors of antibiotic GE 2270 have been isolated, namely factors $B_1$, $B_2$, $C_1$, $C_2$, $D_1$, $D_2$, E and T disclosed in European Patent Application Publication no. 451486 and factor which has as its equivalent, U.S. Pat. No. 5,747,295 $C_{2a}$ is disclosed in European Patent Application Publication no. 529410 which has as its equivalent U.S. Pat. No. 5,514,649. Also degradation products of GE 2270 factor A are known, namely factors $A_1$, $A_2$, $A_3$ and H disclosed in U.S. Pat. No. 5,139,778.

Among these compounds, factor A, $B_2$, $C_1$ and $C_2$ may be employed as suitable starting materials for preparing the compounds of the present invention.

The above factors may be represented by the following formula II:

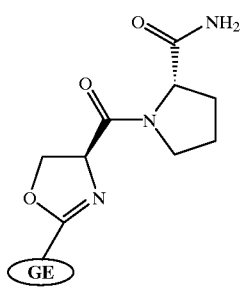

II wherein

is a group as above defined wherein
$W^1$ is phenyl and $W^2$ is hydroxy and
when $X^1$ is $CH_3$ and $X^2$ is $CH_2OCH_3$, factor A is determined;
when $X^1$ is $CH_3$ and $X^2$ is $CH_3$, factor $B_2$ is determined;
when $X^1$ is $CH_3$ and $X^2$ is H, factor $C_1$ is determined; and
when $X^1$ is H and $X^2$ is $CH_2OCH_3$, factor $C_2$ is determined.

It should be noted that this formula does not correspond to the one disclosed in the above cited Patent Applications, which formula was assigned on the basis of the physicochemical data reported therein. As a matter of fact, further studies on the degradation products of the GE2270 factors (P. Tavecchia et al., Jour. of Antib., 47, no. 12 (1994), 1564–1567) have lead to the conclusion that the surmised aminoacid sequence was not correct, as the two aminoacids bearing the moieties $X^1$ and $X^2$ were actually in an opposite sequence in comparison with the formula previously reported; therefore the present formula II has been proposed for correctly representing the structure of antibiotic GE 2270.

A GE 2270-like antibiotic of formula IIa:

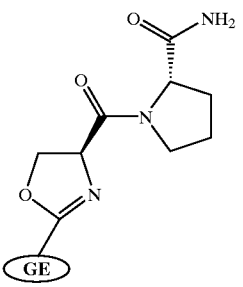

IIa wherein GE is a group as above defined wherein both $W^1$ and $W^2$ are methyl,
$X^1$ is methyl and $X^2$ is hydrogen,
has been described by K. Shimanaka et al., Journal of Antibiotics, vol.47, pp. 668–674 (isolation, physicochemical characteristics, antimicrobial activity) and vol. 47, pp. 1153–1159 (structure elucidation); both these articles are herein incorporated by reference.

Said GE 2270-like antibiotic, named amythiamicin factor A, has been isolated from the fermentation broth of Amycolatopsis sp. MI481-42F4, which strain has been deposited in the National Institute of Bioscience and Human-Technology, Agency of Industrial Science and Technology, Japan, with the accession No. FERM P-12739.

The fermentation of Amycolatopsis sp. MI481-42F4 is conducted according to conventional methodologies in conventional nutrient medium; amythiamicin factor A shows antimicrobial activity against gram positive bacteria. Also this compound may suitably be employed as starting material for the process of the present invention.

In the following of the present specification, with the wording "GE 2270 starting material" is intended any suitable factor of antibiotic GE 2270, such as factor A, $B_2$, $C_1$ and $C_2$, as well as amythiamicin factor A.

Furthermore, amide derivatives of GE 2270 derivatives of general formula

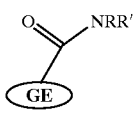

wherein the group GE is as defined in formula II and R and R' have a plurality of meanings, are described in European Patent Application Publication No. 565567 which has as its equivalent, U.S. Pat. No. 5,599,791 (also in this case, for the reasons set forth before, the disclosed structure of the core portion is uncorrect).

As evident, the above amide derivatives of GE 2270 differ from the compounds of the present invention in that the two terminal heterocycle rings of the GE2270 molecule (i.e. the oxazoline and the proline rings) are not present in the above general formula.

In the present description, the terms used above in defining the meanings of the substituents are intended to have the meanings commonly assigned to them in the art. Accordingly:

$(C_1-C_4)$alkyl represents a linear or branched hydrocarbon moiety containing 1, 2, 3 or 4 carbon atoms such as:
—$CH_3$,
—$CH_2$—$CH_3$,
—$CH_2$—$CH_2$—$CH_3$,
—CH—$(CH_3)_2$,
—$CH_2$—$CH_2$—$CH_2$—$CH_3$,
—$CH(CH_3)$—$CH_2$—$CH_3$,
—$CH_2$—$CH(CH_3)$—$CH_3$,
—C—$(CH_3)_3$;

$(C_1-C_4)$alkylene represents a bifunctional linear or branched hydrocarbon moiety containing 1, 2, 3 or 4 carbon atoms such as:
—$CH_2$—,
—$CH_2$—$CH_2$,
—$CH(CH_3)$—
—$CH_2$—$CH_2$—$CH_2$—,
—$CH(CH_3)$—$CH_2$—,
—$CH_2$—$CH_2$—$CH_2$—$CH_2$—,
—$CH(CH_3)$—$CH_2$—$CH_2$—,
—$CH_2$—$CH(CH_3)$—$CH_2$—

—C(CH$_3$)$_2$—CH$_2$—;

(C$_1$–C$_4$)alkylenecarbonyl represents a bifunctional carbonylic moiety containing 2 to 5 carbon atoms, such as:
—CH$_2$—CO—,
—CH$_2$—CH$_2$—CO—,
—CH(CH$_3$)—CO—,
—CH$_2$—CH$_2$—CH$_2$—CO—,
—CH(C$_2$H$_5$) —CO—,
—CH(CH$_3$)—CH$_2$—CO—,
—CH (C$_2$H$_5$)—CH$_2$—CO—,
—CH$_2$—CH$_2$—CH$_2$—CH$_2$—CO—,
—CH(CH$_3$)—CH$_2$—CH$_2$—CO—,
—C(CH$_3$)$_2$—CH$_2$—CO—;

hydroxy(C$_1$–C$_4$)alkylene represents a linear or branched alcanolic moiety of from 1 to 4 carbon atom, such as:
—CH$_2$—OH,
—CH$_2$—CH$_2$—OH,
—CH(CH$_3$)—OH
—CH$_2$—CH$_2$—CH$_2$—OH,
—CH(CH$_3$)—CH$_2$—OH,
—CH$_2$—CH(CH$_3$)—OH
—CH$_2$—CH$_2$—CH$_2$—CH$_2$—OH,
—CH(CH$_3$)—CH$_2$—CH$_2$—OH,
—CH$_2$—CH(CH$_3$)—CH$_2$—OH,
—CH$_2$—CH$_2$—CH(CH$_3$)—OH
—C(CH$_3$)$_2$—CH$_2$—OH;

di(C$_1$–C$_4$)alkylamino, is an amino moiety substituted with two linear or branched alkyl groups containing 1, 2, 3 or 4 carbon atoms such as:
—N—(CH$_3$)$_2$,
—N(CH$_3$) (CH$_2$—CH$_3$),
—N(CH$_2$—CH$_3$)$_2$,
—N(CH$_3$)(CH$_2$—CH$_2$—CH$_3$),
—N(CH$_2$—CH$_3$)(CH$_2$—CH$_2$—CH$_3$),
—N(CH$_2$—CH$_2$—CH$_3$)$_2$,
—N(CH$_3$) [CH—(CH$_3$)$_2$],
—N(CH$_2$—CH$_3$) [CH—(CH$_3$)$_2$],
—N(CH$_3$)(CH$_2$—CH$_2$—CH$_2$—CH$_3$),
—N(CH$_2$—CH$_3$)(CH$_2$—CH$_2$—CH$_2$—CH$_3$),
—N(CH$_2$—CH$_2$—CH$_3$)(CH$_2$—CH$_2$—CH$_2$—CH$_3$),
—N(CH$_2$—CH$_2$—CH$_2$—CH$_3$)$_2$,
—N(CH$_2$—CH$_2$—CH$_2$—CH$_3$) [CH—(CH$_3$)$_2$];

a five or six membered heterocycle ring according to the meanings of R$^2$ or R$^5$ is an heterocycle ring such as:

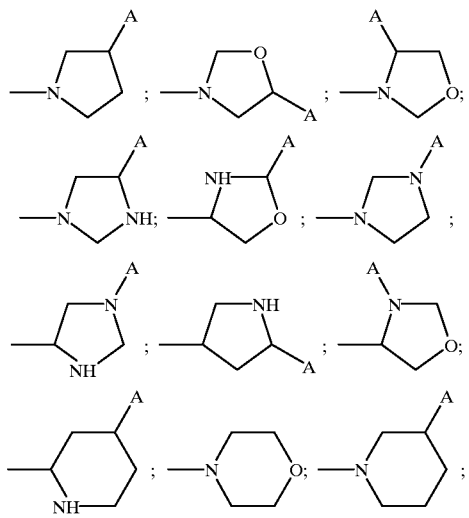

wherein A represents hydrogen or hydroxy(C$_1$–C$_4$)alkylene when referring to the substituent "R$^2$" or A represents only hydrogen when referring to the substituent "R$^5$";

a five or six membered heterocycle ring formed by the moieties R$^1$ and alk-R$^2$ together, is an heterocycle ring such as:

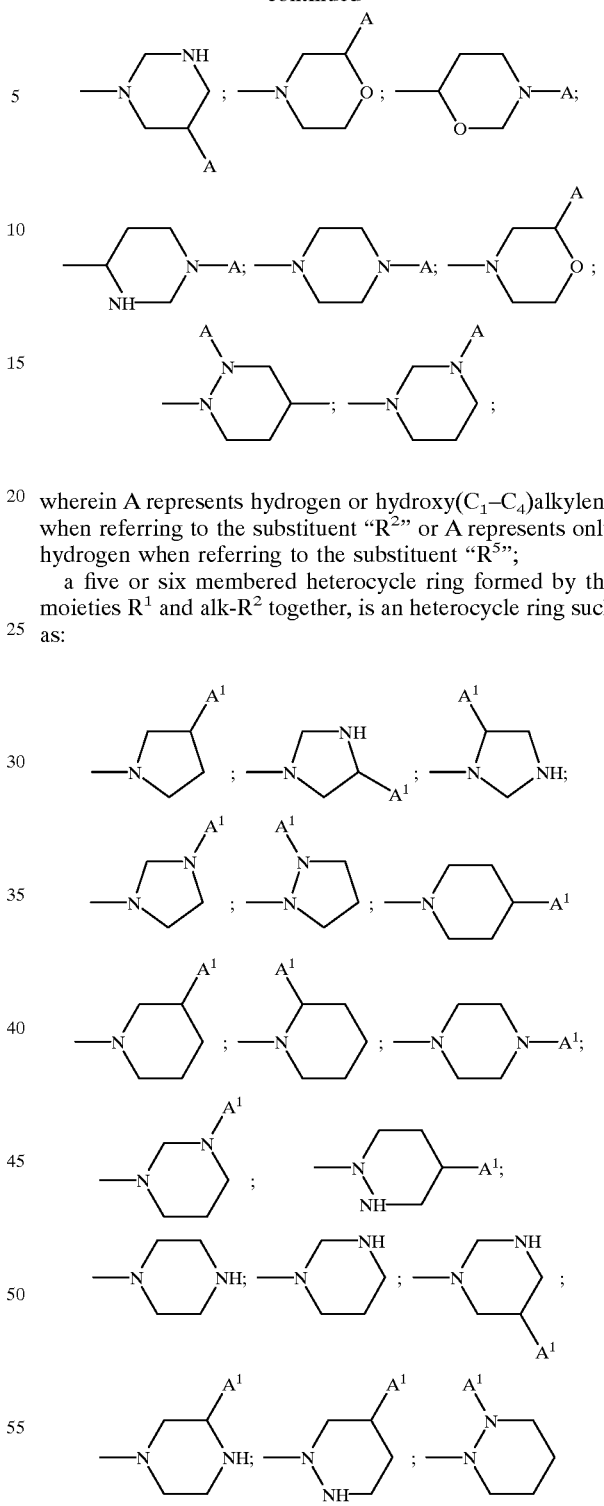

wherein A$^1$ represents hydrogen or the optional substituents of the heterocycle ring as set forth before.

By comparing the above formulas I and II, it appears that GE 2270 factors naturally occur with a determined chirality of the molecule; according to the present invention, the compounds of formula I may be obtained with both the chiralities, with respect to the bond between the oxazoline and the proline rings. Although in most cases, the antimicrobial activity of the two epimers (either of the starting materials or of the compounds of the invention) is almost the same, in some cases, against particular strains (e.g. streptococci), it has been observed a slightly higher antimicrobial activity for those compounds having the chirality corresponding to the natural one.

Thus, a group of preferred compounds of the invention are those compounds of general formula Ia

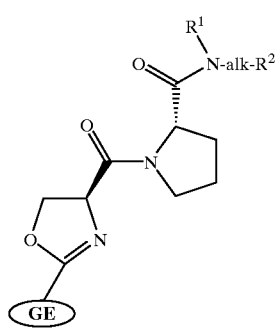

Ia wherein the group GE, $R^1$, alk and $R^2$ are as defined in formula I.

Another group of preferred compounds are those compounds of formula I or Ia wherein the group GE is such that $W^1$ is phenyl, $W^2$ is hydroxy, $X^1$ is methyl, $X^2$ is methoxymethylen and $R^1$, alk and $R^2$ are as defined in formula I.

A further group of preferred compounds are those compounds of formula I or Ia wherein the group GE is as defined in formula I and $R^1$ represents hydrogen or $(C_1-C_4)$alkyl, alk represents $(C_1-C_4)$alkylene or $(C_2-C_5)$alkylene-carbonyl, $R^2$ represents a $NR^3R^4$ group wherein $R^3$ represents $(C_1-C_4)$alkyl and $R^4$ represents $(C_1-C_4)$alkyl or di$(C_1-C_4)$alkylamino-$(C_1-C_4)$alkylene, or a five or six membered heterocycle ring containing one or two nitrogen atoms, optionally substituted with a group selected from $(C_1-C_4)$alkyl and hydroxy$(C_1-C_4)$alkylene;

or $R^1$ and alk-$R^2$ together with the adiacent nitrogen atom form a five or six membered heterocycle ring optionally containing a further nitrogen atom, optionally substituted with a group selected from $(C_1-C_4)$alkyl, di$(C_1-C_4)$alkylamino, di$(C_1-C_4)$alkylamino-$(C_1-C_4)$alkylene and a alk$_2$-$R^5$ group wherein alk$_2$ is $(C_1-C_2)$alkyl and $R^5$ is a $NR^6R^7$ group wherein $R^6$ represents $(C_1-C_4)$alkyl and $R^7$ represents $(C_1-C_4)$alkyl or di$(C_1-C_4)$alkylamino $(C_1-C_4)$alkylene or a five or six membered heterocycle ring containing one or two heteroatoms selected from nitrogen and oxygen.

A further group of preferred compounds are those compounds of formula I or Ia wherein the group GE is as defined in formula I and $R^1$ represents hydrogen or $(C_1-C_2)$alkyl, alk represents $(C_1-C_3)$alkylene or $(C_2-C_3)$alkylenecarbonyl, $R^2$ represents a $NR^3R^4$ group wherein $R^3$ represents $(C_1-C_3)$alkyl and $R^4$ represents $(C_1-C_3)$alkyl or di$(C_1-C_2)$alkylamino-$(C_1-C_2)$alkylene, or a five or six membered heterocycle ring containing one or two nitrogen atoms, optionally substituted with a group selected from $(C_1-C_2)$alkyl and hydroxy$(C_1-C_2)$ alkylene;

or $R^1$ and alk-$R^2$ together with the adiacent nitrogen atom form a five or six membered heterocycle ring optionally containing a further nitrogen atom, optionally substituted with a group selected from $(C_1-C_2)$alkyl, di $(C_1-C_2)$ alkylamino, di$(C_1-C_2)$alkylamino-$(C_1-C_2)$alkylene and a alk$_2$-$R^5$ group wherein alk$_2$ is $(C_1-C_2)$alkyl and $R^5$ is a $NR^6R^7$ group wherein $R^6$ represents $(C_1-C_2)$alkyl and $R^7$ represents $(C_1-C_2)$alkyl or di$(C_1-C_2)$alkylamino $(C_1-C_2)$alkylene or a five or six membered heterocycle ring containing one or two heteroatoms selected from nitrogen and oxygen.

Particularly preferred compounds are those compounds of formula I or Ia wherein the group GE is such that $W^1$ is phenyl, $W^2$ is hydroxy, $X^1$ is methyl, $X^2$ is methoxymethylene and $R^1$ represents hydrogen or $(C_1-C_2)$alkyl, alk represents $(C_1-C_3)$alkylene, $R^2$ represents a $NR^3R^4$ group wherein $R^3$ represents $(C_1-C_3)$alkyl and $R^4$ represents $(C_1-C_3)$alkyl or di$(C_1-C_2)$alkylamino-$(C_1-C_2)$alkylene, or a five or six membered heterocycle ring containing one or two nitrogen atoms, optionally substituted with a group selected from $(C_1-C_2)$alkyl and hydroxy$(C_1-C_2)$ alkylene;

or $R^1$ and alk-$R^2$ together with the adiacent nitrogen atom form a five or six membered heterocycle ring optionally containing a further nitrogen atom, optionally substituted with a group selected from $(C_1-C_2)$alkyl, di$(C_1-C_2)$ alkylamino, di$(C_1-C_2)$alkylamino-$(C_1-C_2)$alkylene and a alk$_2$-$R^5$ group wherein alk$_2$ is $(C_1-C_2)$alkylene and $R^5$ is a $NR^6R^7$ group wherein $R^6$ represents $(C_1-C_2)$alkyl and $R^7$ represents $(C_1-C_2)$alkyl or di$(C_1-C_2)$alkylamino $(C_1-C_2)$alkylene or a five or six membered heterocycle ring containing one or two heteroatoms selected from nitrogen and oxygen.

Examples of —N($R^1$)alk$R^2$ groups, as defined in formula I, are the following:

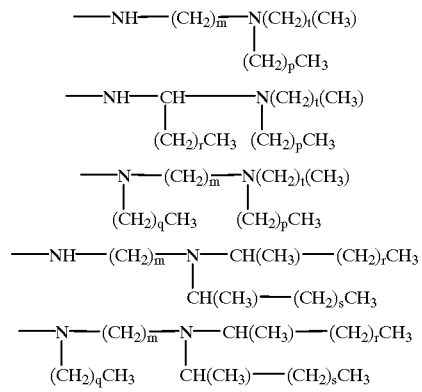

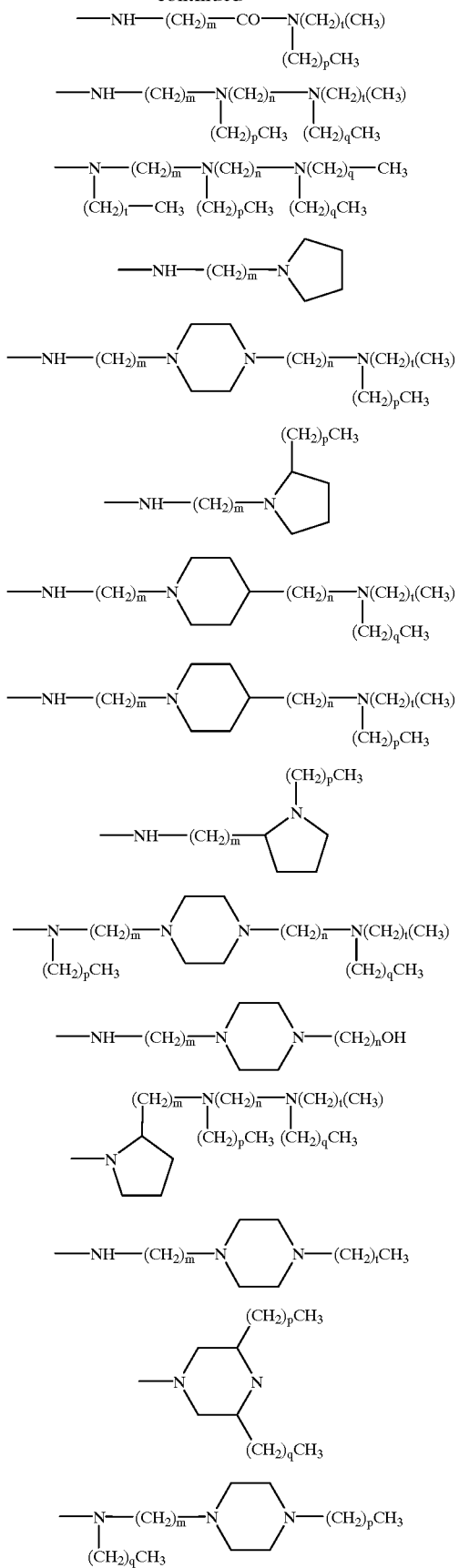
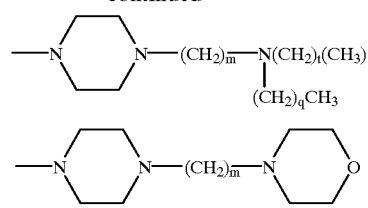
wherein:
m and n=1, 2, 3 or 4;
p, q and t=0, 1, 2 or 3
r and s=0 or 1.
Preferred examples of —N(R$^1$)alkR$^2$ groups are the following:
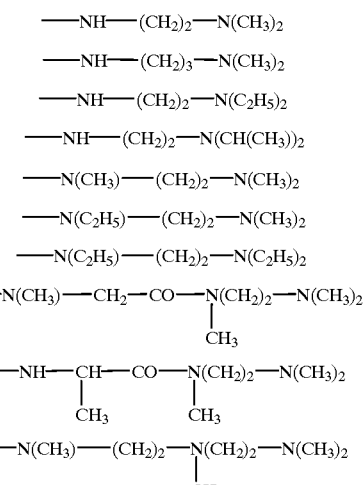
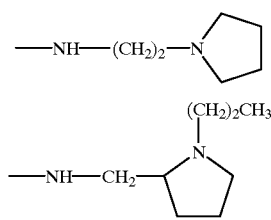
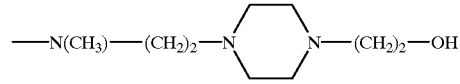
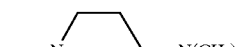
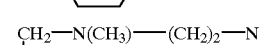
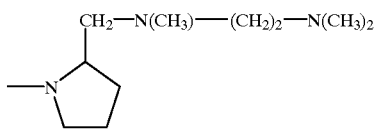

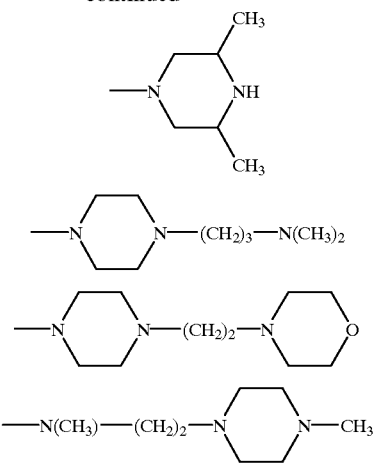

The compounds of the invention can form salts according to conventional procedures.

In particular, those compounds of formula I wherein the group —N(R$^1$)alkR$^2$ contains further amine functions can form acid addition salts.

Preferred addition salts of the compounds of this invention are the pharmaceutically acceptable acid addition salts.

With the term "pharmaceutically acceptable acid addition salts" are intended those salts with acids which from biological, manufacturing and formulation standpoint are compatible with the pharmaceutical practice as well as with the use in the animal growth promotion.

Representative and suitable acid addition salts of the compounds of formula I include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, dodecylsulfonic (estolic), benzenesulfonic, sorbic, picric, benzoic, cinnamic acid and the like.

The transformation of the free amino or non-salt compounds of the invention into the corresponding addition salts, and the reverse, i.e. the transformation of an addition salt of a compound of the invention into the non-salt or free amino form, are within the ordinary technical skill and are encompassed by the present invention. The only precaution is to avoid solutions with pH lower than 4–5 when preparing the addition salt (for avoiding the opening of the oxazolinic ring) and solutions with a pH higher than 8–9 when freing the base (for avoiding epimerization on the chiral center).

For instance, a compound of formula I can be transformed into the corresponding acid addition-salt by dissolving the non-salt form in an aqueous solvent and adding a slight molar excess of the selected acid. The resulting solution or suspension is then lyophilized to recover the desired salt. Instead of lyophilizing, in some instances, it is possible to recover the final salt by extraction with an organic solvent, concentration to a small volume of the separated organic phase and precipitation by adding a non-solvent.

In case the final salt is unsoluble in an organic solvent where the non-salt form is soluble, it may be recovered by filtration from the organic solution of the non-salt form after addition of the stoichiometric amount or a slight molar excess of the selected acid.

The non-salt form can be prepared from a corresponding acid salt dissolved in an aqueous solvent which is then neutralized to free the non-salt form. This is then recovered for instance by extraction with an organic solvent or is transformed into another acid addition salt by adding the selected acid and working up as above.

A common desalting procedure may be employed when, following the neutralization, desalting is necessary.

For example, column chromatography on controlled pore polydextrane resins (such as Sephadex LH 20) or silanized silica gel may be conveniently used. After eluting the undesired salts with an aqueous solution, the desired product is eluted by means of linear gradient or step-gradient of a mixture of water and a polar or apolar organic solvent, such as acetonitrile/water from 50:50 to about 100% acetonitrile.

As is known in the art, the salt formation either with pharmaceutically acceptable acids or non-pharmaceutically acceptable acids may be used as a convenient purification technique. After formation and isolation, salt form of a compound of formula I can be transformed into the corresponding non-salt or into a pharmaceutically acceptable salt.

In some instances the acid addition salt of a compound of formula I is more soluble in water and hydrophilic solvents and has an increased chemical stability. Good solubility and stability in water or hydrophylic solvents of an active compound are in general appreciated in the art, for the preparation of suitable pharmaceutical compositions for the administration of the medicament.

However, in view of the similarity of the properties of the compounds of formula I and their salts, what is said in the present application when dealing with the biological activities of the compounds of formula I applies also to their pharmaceutically acceptable salts, and viceversa.

A suitable method for preparing the compounds of the invention (hereinafter defined as "Method A") comprises reacting a compound of formula III

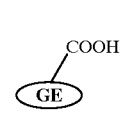

III wherein the group GE is as defined in formula I, with a suitable serinamide of formula IV:

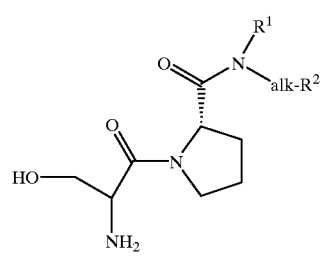

IV wherein R$^1$, alk and R$^2$ are as in formula I, in an inert aprotic organic solvent in the presence of a condensing agent;

b) cyclizing the serine moiety of the obtained compound of formula IIIa

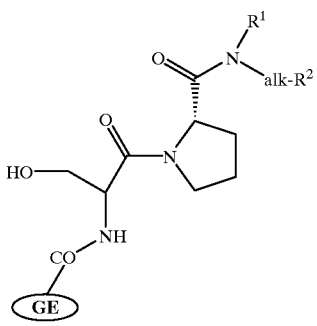

IIIa with a suitable cyclizing reactant, in order to obtain the desired compound of formula I.

According to method A, the chirality of the final compound is determined by the chirality of the serinamide reactant employed, with retention of the configuration of the serine chiral center. Thus, for obtaining the amide derivatives with a chirality corresponding to the natural one, L-serinamides shall be employed.

Inert organic aprotic solvents useful for the condensation reaction according to method A are those solvents which do not unfavorably interfere with the reaction course and are capable of at least partially solubilizing the antibiotic starting material.

Examples of said solvents are organic amides, ethers of glycols and polyols, phosphoramides, sulfoxides and mitures thereof. Preferred examples are: dimethylformamide, dimethoxyethane, hexamethylphosphoramide, dimethylsulfoxide, dioxane, and mixtures thereof. Preferably, dimethylformamide (DMF) is employed.

The condensing agent in the present method is one suitable for forming amide bonds in organic compounds and in particular in peptide synthesis.

Representative and preferred examples of condensing agents are $(C_1-C_4)$alkyl, phenyl or heterocyclic phosphorazidates such as, diphenyl-phosphorazidate (DPPA), diethyl-phosphorazidate, di(4-nitrophenyl)-phosphorazidate, dimorpholyl-phosphorazidate and diphenylphosphorochloridate or benzotriazol-1-yl-oxy-tripyrrolidinophosphoniumhexa-fluorophosphate (PyBOP). The preferred condensing agent is DPPA.

The condensing agent is generally employed in a slight molar excess, such as from 1.1 to 1.5; preferably the molar excess of condensing agent is 1.2 times the amount of antibiotic GE 2270 starting compound.

According to the present method, the serinamide of formula IV is normally used in a slight molar excess.

In general, a 1 to 1.5 fold molar excess is used, while a 1.2 fold molar excess is preferred.

For the amidation to proceed, it is necessary that the serinamide of formula IV be capable of forming a salt with the carboxy function of the antibiotic starting material. As this could require the use of a higher amount of the serinamide, in such a case it is convenient to add a salt-forming base to the reaction mixture, at least in an equimolecular amount, and preferably a 2 to 3 fold molar excess, with respect to the antibiotic starting material.

Examples of said salt-forming bases are tertiary organic aliphatic or alicyclic amines such as trimethylamine, triethylamine (TEA), N-methyl pyrrolidine or heterocyclic bases such as picoline, and the like.

In addition, the serinamide of formula IV may also conveniently be introduced in the reaction medium as a corresponding acid addition salt, such as hydrochloride, trifluoroacetate, and the like. In fact, at least in some instances, the use of the salified serinamide of formula IV, which is then freed in situ with the above mentioned bases, is preferred, particularly when the salt is more stable than the corresponding free amine. In this case, at least a double molar proportion and preferably a 2 to 3 fold molar excess of a base capable of freeing the serinamide of formula IV from its salts, is used. Also in this case, the suitable base is a tertiary organic aliphatic or alicyclic amine like those exemplified above, preferably TEA.

The reaction temperature will vary considerably depending on the specific starting materials and reaction conditions. In general, it is preferred to conduct the reaction at temperatures from 0° C. to room temperature, preferably starting at about 0° C. and allowing the mixture to reach room temperature during the reaction.

Also the reaction time varies considerably depending on the other reaction parameters; in general the condensation is completed in about 5–24 h.

Generally, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques. For instance the reaction mixture may be poured into an aqueous basic solution for precipitating the compound of formula IVa as an addition salt. The basic solution should have a pH suitable for precipitating the salt of the desired compound, without modifying its chemical structure. In general, the pH ranges from 8 to 10, and is obtained with an aqueous solution of an inorganic base, such as alkali or alkaline-earth metal hydroxides, carbonates, bicarbonates, and the like. The compound of formula IVa is obtained as a crude, after filtration and evaporation of the above basic solution, as the purification step is preferably accomplished after the cyclization reaction. However, when a purified product is desired, the known per se separation and purification techniques may be employed, which include, for instance, extraction with solvents, precipitation by pH modification, precipitation by addition of non-solvents, etc., in conjunction with further separations and purifications by column chromatography.

Step b) of the present process, i.e. the serine-oxazoline cyclization is performed according to methods known per se in the art.

According to a preferred embodiment, the compound of formula IIIa is reacted with methoxycarbonylsulfamoyltriethylammonium hydroxide, inner salt (Burgess reagent), and the reaction mixture is then refluxed for obtaining th oxazoline cyclization.

More in detail, the obtained compound of formula IIIa is reacted with an excess (about 3:1 to 15:1) of Burgess reagent, in the presence of an organic aprotic oxygenated solvent, for obtaining the corresponding sulfamoyl ester of the Burgess reactant.

Examples of organic aprotic oxygenated solvents are saturated linear or cyclic ethers or glycol ethers. Preferred examples of said solvents are tetrahydrofuran (THF), dioxane. Optionally chlorinated solvents may also be added to the reaction mixture, such as dichloromethane ($CH_2Cl_2$), chloroform, for increasing the solubility of the reactants.

Optionally, a base may also be added to the reaction mixture, for avoiding undesired side-reactions. Examples of suitable bases are tertiary organic aliphatic or alicyclic amines such as trimethylamine, triethylamine (TEA), N-methyl pyrrolidine or heterocyclic bases such as picoline, and the like; preferably TEA is employed.

The reaction temperature will vary considerably depending on the specific starting materials and reaction conditions. In general, it is preferred to conduct the reaction at temperatures of from 18° C. to 30° C., preferably at room temperature.

Also the reaction time varies considerably depending on the other reaction parameters; in general the reaction is completed in about 4 to 20 hours.

Generally, the reaction course is monitored by TLC or preferably by HPLC according to methods known in the art.

After the reaction is completed, a secondary or tertiary alcohol is added to the reaction mixture, for quenching the reaction. Said alcohol should be able to react with the unreacted Burgess reactant and be transformed in olefinic compounds, preferably low boiling olefines. Thus, a secondary or tertiary $(C_3-C_5)$alcohol may suitably be employed, such as isopropanol, tert-butanol, 1-methyl-propanol, 1,1-dimethyl-propanol, 1,2-dimethyl-propanol, 1-ethyl-propanol; preferably, isopropanol is employed.

The reaction mixture is then refluxed for cyclizing the oxazoline. Time and temperature of the reflux will vary mainly depending on the solvents present in the reaction mixture. For instance, if low boiling solvents (e.g. alcohols, chlorinated solvents) are removed before refluxing, higher reflux temperatures are obtained. Thus, depending on the type of solvents present in the refluxing mixture, the temperature will vary from 50° C. to 80° C. In general, as the higher the reflux temperature, the shorter the time, the reflux time will accordingly vary from 20 to 5 hours.

Also in this case, the reaction course is monitored by TLC or preferably by HPLC according to methods known in the art. On the basis of the results of these assays a man skilled in the art will be able to decide when to stop the reflux and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent), reverse phase chromatography or chromatography on neutral aluminium oxide (using dichloromethane/methanol mixtures as eluent).

The starting material of formula III wherein the group GE is such that $W^1$ is phenyl, $W^2$ is hydroxy, $X^1$ is methyl and $X^2$ is methoxymethylene, corresponding to antibiotic GE 2270 factor $A_3$, and the hydrolysis process for preparing it, are disclosed in U.S. Pat. No. 5,139,778.

Generally, the above mentioned hydrolytic conditions involve the use of mixtures of buffered or unbuffered aqueous acid media and polar organic solvents. The reaction temperature varies depending on factors such as the strength and the concentration of the acid employed, and is generally comprised between −10° C. and 90° C. Also the reaction time varies considerably depending on parameters such as the temperature, the acid strength and its concentration; generally, it may vary from a few minutes to several hours.

In general, when milder hydrolysis conditions are employed, e.g. shorter reaction time and lower temperature or lower acid strength or concentration, antibiotic GE 2270 factor $A_1$ is normally obtained, while stronger hydrolysis conditions yield antibiotic GE 2270 factor $A_2$. To obtain antibiotic GE 2270 factor $A_3$, still more drastic hydrolysis conditions are necessary. Factor $A_2$ may also be converted into factor $A_3$ by basic hydrolysis with diluted alkali.

By following the above procedure, but starting from GE 2270 factor $B_2$, $C_1$, $C_2$ or amythiamicin factor A instead of GE2270 factor A, the respective starting materials of formula III are obtained.

The serinamide of formula IV is prepared according to known per se techniques of peptide synthesys, described in a number of references books like E. Gross and J. Meienhofer "The Peptides", Vol. 3, Academic Press, New York, 1981 and M. Bodanszky and A. Bodanszky "The Practice of Peptide Synthesis, Springer-Verlag, Berlin Heidelberg, 1984.

As a general procedure, a N-protected L-proline is first reacted with the desired amine of formula IVa

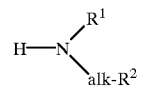

IVa wherein $R^1$, alk, and $R^2$ are as defined in formula I; the obtained L-prolinamide is then deprotected and reacted with a N-protected serine, to give the desired N-protected starting material. As said above, when amide derivatives of formula I with a chirality corresponding to the natural one are desired, L-serinamides shall be employed; accordingly, the prolinamide shall be reacted with N-protected L-serine.

As known in the the art, the amidation reactions may either be performed in the presence of a condensing agent (e.g. phosphorazidates such as diphenilphosphorazidate, DPPA) or the N-protected amino acid may be reacted in the form of an activated ester (such as pentafluorophenyl, N-hydroxysuccynimide or 1-hydroxybenzothiazole ester)

The protecting group employed in both steps of the above described process are those generally employed in peptides synthesis. Preferably, the N-protection of serine is performed with protecting group which are easily removable under acid or neutral hydrolitic conditions, such as t-butoxycarbonyl (BOC) or benzyloxycarbonyl (cbz).

Preferably, the N-deprotection of the serinamide is performed only short before the amidation reaction with the GE2270 starting material, so to avoid the formation of undesired side products.

The amine of general formula IVa is either a commercially available compound or is prepared according to known per se techniques, described in a number of references books, such as "Comprehensive Organic Synhthesis, vol. 8, 1991, Pergamon Press".

Another method (hereinafter defined as "Method B") for preparing the compounds of the invention is to react a compound of formula V

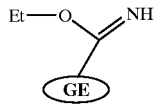

V wherein the group GE is as defined in formula I, with a serinamide of formula IV as above defined, in a protic organic solvent.

Also in this case as in method A, the chirality of the final compound is determined by the chirality of the serinamide reactant employed, with retention of the configuration of the serine chiral center.

Preferred protic organic solvents are those solvents which do not unfavourably interfere with the reaction course and are capable of at least partially solubilizing the antibiotic starting material. Preferred examples of such solvents are ($C_1$–$C_4$)alcohols, such as methanol, ethanol, propanol, iso-propanol, butanol, iso-butanol and mixtures thereof.

Preferably, also minor amounts of an aprotic organic solvent are added, for increasing the solubility of the GE 2270 starting material; preferred solvents are in this case chlorinated solvents, particularly preferred being dichloromethane.

Furthermore, as the serinamide of formula IV is preferably employed in the form of acid addition salt, a base as defined before is preferably added to the reaction mixture. The total amount of base will depend on the number of salified aminic groups of serinamide; as a general rule, if "n" is the number of equivalents of salified aminic groups, then about "n–1" equivalents of base are added.

Examples of said bases are, as above, tertiary organic aliphatic or alicyclic amines such as trimethylamine, triethylamine (TEA), N-methyl pyrrolidine or heterocyclic bases such as picoline, and the like, preferred being TEA.

The reaction temperature will vary considerably depending on the specific starting materials and reaction conditions. In general, it is preferred to conduct the reaction at temperatures of from 15° C. to 30° C., conveniently at room temperature.

Also the reaction time varies considerably depending on the other reaction parameters; in general the condensation is completed in about 20–40 h.

Generally, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent), reverse phase chromatography or chromatography on neutral aluminium oxide (using dichloromethane/methanol mixtures as eluent).

A suitable method for preparing the starting material of formula V is as described in European Patent Application no. 565567 which has as its equivalent, U.S. Pat. No. 5,599,791, here incorporated by reference. Antibiotic GE 2270 factor $A_2$ (prepared as described in the above cited U.S. Pat. No. 5,139,778), or the corresponding derivatives of GE2270 factor $B_2$, $C_1$, $C_2$ or amythiamicin factor A, is reacted with ammonia in the presence of an organic protic solvent, preferably ($C_1$–$C_4$)alcohol, particularly preferred being methanol. After about 2 to 4 days, preferably 3 days, the solution is evaporated and the residue is worked up according to the above known per se techniques, thus obtaining the respective amide derivative of formula:

The obtained compound is in turn reacted with a solution of Burgess reagent in an organic aprotic solvent. Suitable solvents are cyclic or glycol ethers such as THF or dioxane or chlorinated solvents such as dichloromethane ($CH_2Cl_2$) or chloroform, or mixtures thereof; preferably a mixture of THF/$CH_2Cl_2$ is employed.

Furthermore, a base is optionally added to the reaction mixture, as previously described; preferably triethylamine is employed.

Optionally, further Burgess reagent may be added to the reaction mixture after 12 to 20 hours, preferably after 16 hours.

The reaction temperature, depending on the other reaction parameters, may vary from 18° C. to 30° C., preferably at room temperature.

Also the reaction time varies considerably depending on the other reaction parameters; in general the reaction is completed in about 12 to 36 hours after the last addition of Burgess reagent.

Generally, the reaction course is monitored by TLC or preferably by HPLC according to methods known in the art. On the basis of the results of these assays a man skilled in the art will be able to decide when to stop the reaction and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent).

The corresponding nitrile derivative of formula

is thus obtained, which is then dissolved in ethanol, preferably in the presence of a chlorinated co-solvent (e.g. dichloromethane, chloroform), and the solution is cooled at about 0° C.; dry HCl is then bubbled through the solution for from 4 to 8 hours, preferably for 6 hours.

The reaction mixture is preferably allowed to stay at about 4° C. for from 10 to 18 hours, and then poured into a buffering basic solution for neutralizing the excess of HCl; such solution, having a pH lower than 10, is generally a phosphate or carbonate buffer, preferably a carbonate buffer, particularly preferred being a saturated aqueous solution of sodium carbonate.

The solid which precipitates is worked up according to the above known per se techniques, thus obtaining the desired starting material of formula V.

A further method for preparing the compounds of the invention (hereinafter defined as "Method C") is to react a compound of formula VI

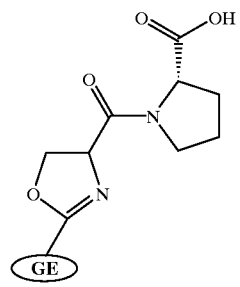

wherein the group GE is as defined in formula I, with an amine of general formula IVa:

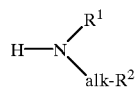

IVa wherein $R^1$, alk, and $R^2$ are as defined in formula I, in the presence of an inert organic solvent and of a condensing agent.

Useful inert organic aprotic solvents are as defined for method A.

Also type and amounts of condensing agent are those defined for the condensation reaction of method A.

The starting material of formula VI is preferably used in its salified form, preferably as an alkali metal salt, particularly preferred being the sodium salt. Thus, a strong acid is conveniently added to the reaction mixture, for freeing the compound from its salt; in general a 2 fold excess of acid equivalents are preferably added. Examples of strong acids are hydrohalide acids or sulfuric acid; preferred beeing hydrochloric acid.

As above, a salt-forming base is preferably added to the reaction mixture; type and amount of such base will vary depending on the parameters defined above (i.e. amount of reacting amine and use of salified amine), as well as on the presence of the above defined strong acid; if said acid is present, at least an equivalent amount of base for each equivalent of acid is further added to the reaction mixture.

The reaction temperature will vary considerably depending on the specific starting materials and reaction conditions. In general, it is preferred to conduct the reaction at temperatures between 15° and 30° C., conveniently at room temperature.

Also the reaction time varies considerably depending on the other reaction parameters. In general the condensation reaction is completed in about 10–16 h.

Generally, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent), reverse phase chromatography or chromatography on neutral aluminium oxide (using dichloromethane/methanol mixtures as eluent).

A suitable method for preparing the starting material of formula VI is to react a solution of the starting material of general formula V in ethanol, preferably in the presence of a chlorinated co-solvent (e.g. dichloromethane, chloroform), with a L-serine ($C_1$–$C_4$)alkyl ester salt, preferably methyl ester hydrochloride. The reaction temperature will vary from 15° C. to 30° C., preferably about room temperature, for a time reaction of from 3 to 5 days, preferably about 4 days.

The reaction mixture is then worked up according to known per se techniques, and the solid obtained is purified by means of known chromatographic techniques, preferably by chromatography on silica gel, thus obtaining the compound of formula:

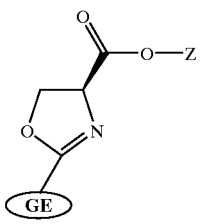

wherein Z represents ($C_1$–$C_4$)alkyl.

The above compound is then dissolved in an inert organic solvent (e.g. alkylamides, alkylnitriles, saturated linear or cyclic ethers, glycol ethers, phosphoramides, chlorinated solvents or mixtures thereof; preferably dioxane) and hydrolyzed with a strong base, such as an alkali or alkaline-earth metal hydroxide, preferably sodium hydroxide, obtaining the corresponding carboxylic acid sodium salt, which may be recovered according to known per se techniques, for instance by addition of non-solvents, preferably ethyl ether.

The obtained compound, which after the hydrolysis is now a mixture of the two epimers, is then reacted with L-proline ($C_1$–$C_4$)alkyl ester, preferably methyl ester, in an inert aprotic organic solvent in the presence of a condensing agent; organic solvent and condensing agent are as previously defined in the condensation reaction of method A.

Optionally, a salt-forming base and a strong acid as above defined are also added to the reaction mixture. The reaction temperature will vary from 15° C. to 30° C., preferably about room temperature, for a time reaction of from 10 to 16 hours. The reaction mixture is then worked up according to known per se techniques and the solid obtained is purified by means of known chromatographic techniques, preferably by means of flash chromatography, thus obtaining the compound of formula wherein Z' represents ($C_1$–$C_4$)alkyl.

The obtained compound is finally dissolved in an organic solvent (e.g. alkylamides, alkylnitriles, saturated linear or cyclic ethers, glycol ethers,

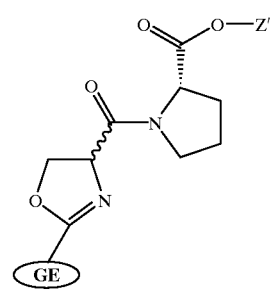

phosphoramides, chlorinated solvents or mixtures thereof; preferably dioxane) and hydrolyzed with a strong base, such as an alkali or alkaline-earth metal hydroxide, preferably sodium hydroxide, obtaining the corresponding carboxylic acid sodium salt, which may be recovered according to known per se techniques, for instance by addition of non-solvents, preferably ethyl ether.

The so obtained starting material is in general a mixture of two epimers. This mixture may be separated or employed as such for the condensation reaction with the amine, thus obtaining an epimeric mixture of the compounds of the invention.

If desired, the epimeric mixture may be separated (either before or after the condensation reaction) according to known per se techniques, such as by reverse phase HPLC, chromatography on neutral or basic aluminium oxide or HPLC on chiral phases.

The following table lists the structural formula of some representative compounds of the invention, for which antimicrobial activity and preparation methodology are given in the following of the specification. The core portion, i.e. the group GE, of all the compounds corresponds to antibiotic GE2270 factor A. All the compounds are intented as enantiomeric mixtures (R,S enantiomers), except compound 3s, which corresponds to the S enantiomer.

| Compound No. | —N(R¹)(alk-R²) group |
|---|---|
| 1 | 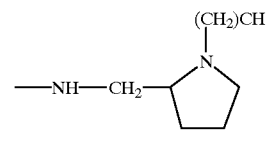 —NH—CH₂—N(pyrrolidine with (CH₂)CH₃) |
| 2 | 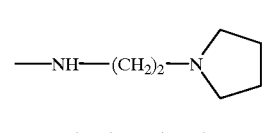 —NH—(CH₂)₂—N(pyrrolidine) |
| 3 and 3s | —NH—(CH₂)₂—N(C₂H₅)₂ |
| 4 | —NH—(CH₂)₃—N(CH₃)₂ |
| 5 | —N(CH₃)—(CH₂)₂—N(CH₃)₂ |
| 6 | 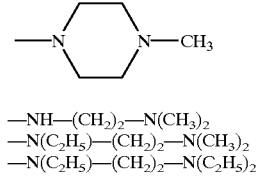 —N(piperazine)—N—CH₃ |
| 7 | —NH—(CH₂)₂—N(CH₃)₂ |
| 8 | —N(C₂H₅)—(CH₂)₂—N(CH₃)₂ |
| 9 | —N(C₂H₅)—(CH₂)₂—N(C₂H₅)₂ |
| 10 | 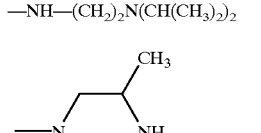 —N(piperazine)—N—N(CH₃)₂ |
| 11 | —NH—(CH₂)₂N(CH(CH₃)₂)₂ |
| 12 | 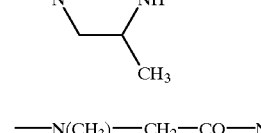 |
| 13 | —N(CH₃)—CH₂—CO—N(CH₂)₂—N(CH₃)₂ with CH₃ |
| 14 | —NH—CH(CH₃)—CO—N(CH₂)₂—N(CH₃)₂ with CH₃ |
| 15 | —N(CH₃)—(CH₂)₂—N(CH₂)₂—N(CH₃)₂ with CH₃ |
| 16 | 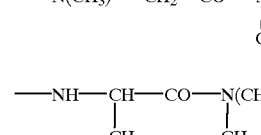 |
| 17 | 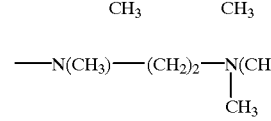 |
| 18 |  |
| 19 | 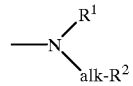 |
| 20 | 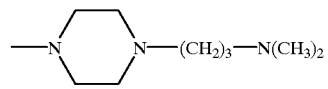 |

The antimicrobial activity of the compounds of the invention can be demonstrated by a series of standard tests in vitro.

The minimal inhibitory concentration (MIC) has been determined by microbroth dilution methodology, in the presence of 0.01% (w/v) of bovine serum albumin (BSA). BSA is added to the diluent to avoid possible adherence of the compounds of the invention to the plastic surface of the microtiter wells, as disclosed also by B. Goldstein et al., Antimicrobial Agents and Chemotherapy, 37 (1993), 741–745.

Inocula were $10^4$ CFU/ml, except for *Propionibacterium acnes* and *Bacteroides fragilis* ($10^5$ CFU/ml).

MICs were read after 18–24 h, except for *Haemophilus influenzae, P. acnes, B. fragilis* (48 h).

All microorganisms were incubated at 37° C.; *H. influenzae* in a 5% $CO_2$ atmosphere, anaerobes in a $N_2$—$CO_2$—$H_2$ (80:10:10) mixture; other organisms in air.

The growth media are: Oxoid Iso-Sensitest broth for staphylococci and *Enterococcus faecalis*); Difco Todd Hewitt broth for streptococci; Difco brain heart infusion broth+1% Difco Supplement C for *H. influenzae;* Difco Wilkins-Chalgren broth for anaerobes.

MICs for some microorganisms are reported below in Table I.

TABLE 1

| STRAIN | Internal code | MIC of the compounds (μg/ml) | | | | | | | | | | |
|---|---|---|---|---|---|---|---|---|---|---|---|---|
| | | 1 | 2 | 3 | 3s | 4 | 5 | 6 | 7 | 8 | 9 | 10 |
| Staphylococcus aureus | L165 | 0.06 | 0.06 | 0.03 | 0.06 | 0.06 | 0.06 | 0.13 | 0.06 | 0.06 | 0.06 | 0.13 |
| Staph. epidermidis ATCC 12228 | L147 | n.t. | n.t. | 0.13 | 0.13 | n.t. | n.t. | n.t. | n.t. | n.t. | n.t. | n.t. |
| Staph. haemolyticus | L602 | n.t. | n.t. | 0.13 | 0.13 | n.t. | n.t. | n.t. | n.t. | n.t. | n.t. | n.t. |
| Streptococcus pyogenes | L49 | 0.5 | 0.5 | 0.5 | 0.25 | 4 | 1 | 2 | 1 | 4 | 8 | 4 |
| Strept. pneumoniae | L44 | 0.13 | 0.13 | 0.13 | 0.13 | 0.25 | 0.25 | 0.25 | 0.13 | 0.25 | 0.5 | 0.25 |
| Strept. sanguis | L1721 | 0.25 | 0.25 | 0.25 | 0.13 | 0.5 | 0.25 | 0.5 | 0.5 | 0.5 | 2 | 0.5 |
| Strept. agalactiae | L310 | n.t. | n.t. | n.t. | 0.5 | 4 | n.t. | n.t. | 4 | 8 | 8 | 8 |
| Enterococc. faecalis ATCC 7080 | L149 | n.t. | n.t. | 0.03 | 0.06 | n.t. | n.t. | n.t. | n.t. | n.t. | n.t. | |
| Propionibact. acnes ATCC 6919 | L1014 | n.t. | n.t. | 0.03 | 0.03 | n.t. | n.t. | n.t. | n.t. | n.t. | n.t. | |
| Bacteroides fragilis ATCC 25285 | L1011 | n.t. | n.t. | 8 | 8 | n.t. | n.t. | n.t. | n.t. | n.t. | n.t. | |
| Haemoph. influenzae ATCC 19418 | L970 | >16 | >16 | 8 | 8 | n.t. | 128 | 128 | n.t. | n.t. | n.t. | |

| STRAIN | Internal code | MIC of the compounds (μg/ml) | | | | | | | | | |
|---|---|---|---|---|---|---|---|---|---|---|---|
| | | 11 | 12 | 13 | 14 | 15 | 16 | 17 | 18 | 19 | 20 |
| Staphylococcus aureus | L165 | 0.06 | 0.06 | 0.13 | 0.13 | 0.06 | 0.13 | 0.06 | 0.06 | 0.06 | 0.13 |
| Staph. epidermidis ATCC 12228 | L147 | n.t. | n.t. | n.t. | n.t. | n.t. | n.t. | n.t. | n.t. | n.t. | n.t. |
| Staph. haemolyticus | L602 | n.t. | n.t. | n.t. | n.t. | n.t. | n.t. | n.t. | n.t. | n.t. | n.t. |
| Streptococcus pyogenes | L49 | 4 | 2 | 4 | 2 | 8 | 4 | 4 | 8 | 0.5 | 4 |
| Strept. pneumoniae | L44 | 0.25 | 0.25 | 0.5 | 0.13 | 1 | 0.5 | 0.5 | 0.5 | 0.25 | 0.5 |
| Strept. sanguis | L1721 | 0.5 | 0.25 | 1 | 0.25 | 2 | 1 | 0.5 | 2 | 2 | 1 |
| Strept. agalactiae | L310 | 4 | 2 | 8 | 4 | 16 | 8 | 8 | 8 | 16 | 8 |

Compound 3s has also been tested on a number of clinical isolates. Against staphylococci isolates, the MIC was never higher than 0.5 μg/ml; against streptococci isolates, the MIC was never higher than 1.0 μg/ml; against enterococci isolates, the MIC was never higher than 0.13 μg/ml.

The antimicrobial activity of the compounds of the invention is confirmed also in experimental septicemia in the mouse.

Control and treatment groups contain ten CD-1 mice (Charles River) weighing 18–22 g.

Two groups of immunocompetent mice are infected intraperitoneally with 0.5 ml of bacterial suspension prepared by diluting an overnight culture of *S. aureus* (L819) or *S. pyogenes* (L49) with sterile peptonized saline, while one group of neutropenic mice is infected intraperitoneally with 0.5 ml of bacterial suspension prepared by diluting an overnight culture of or *E. faecalis* (L1139) with sterile peptonized saline.

Inocula are adjusted so that untreated animals died of septicemia within 48 h. The compound to be tested is administered intravenously once, immediately after infection with *S. aureus*, or twice, immediately and 5 hours after infection with *S. pyogenes* or *E. faecalis*. On the 7th day, the $ED_{50}$ in mg/kg is calculated by the method of Spearman and Kräber (D. J. Finney "Statistical Methods in Biological Assay", Griffin, page 524, 1952) from the percentage of surviving animals at each dose.

The $ED_{50}$ (mg/kg/dose) for compound 3s was as follows:

| $ED_{50}$ for compound 3s in experimental septicemia | |
|---|---|
| Strain | $ED_{50}$ |
| S. aureus (L819) | 1.5 |
| S. pyogenes (L49) | 7 |
| E. faecalis (L1139) | 0.67 |

In view of their properties, the compounds of the invention can be used as active ingredients in the preparation of medicaments for human or animal treatment.

In particular, the amide derivatives of antibiotic GE 2270 of formula I are antimicrobial agents mainly active against gram positive bacteria.

The main therapeutic indication of the antibiotic substances of the invention is thus in the treatment of infections related to the presence of microorganisms susceptible to them.

The term "treatment" is intended to encompass also prophylaxis, therapy and cure.

The patient receiving this treatment is any animal in need, including primates, in particular humans, and other mammals such as equines, cattle, swine, sheep, poultry and pets in general.

The compounds of the invention can be administered as such or in admixture with pharmaceutically acceptable carriers and can also be administered in conjunction with other antimicrobial agents. Conjunctive therapy, thus includes sequential, simultaneous and separate administration of the active compounds in a way that the therapeutical effects of the first administered one is not entirely disappeared when the subsequent is administered.

The dosage of the active ingredient depends on many factors which include type, age and conditions of the patient, specific active ingredient and formulation selected for administration, administration schedule, etc.

Experimental tests for determining the sensitivity of the microorganisms isolated from the patient may also offer useful indication to select the appropriate dosage.

In general, effective antimicrobial dosages are employed per single unit dosage form.

Repeated applications of these dosage forms, e.g. from 2 to 6 times a day, are in general preferred. An effective dosage may be in general in the range 0.5–50 mg/kg body weight/day.

Anyway, the prescribing physician will be able to determine the optimal dosage for a given patient in a given situation.

The compounds of the invention can be formulated into formulation suitable for parenteral administration containing a liquid vehicle, according to procedures known per se in the art. Examples of suitable vehicles for preparing injectable dosage forms of the compounds of the invention are water, aqueous vehicles (e.g. Dextrose injections), water miscible solvents (e.g. ethyl alcohol, polyethylene glycol, propylene glycol, etc.) and non-aqueous vehicles (e.g. "fixed oils" such as corn oil, cottonseed oil, peanut oil and sesame oil). Optionally, the injectable preparation may further contain surface-active agent (e.g. polyoxyethylene sorbitan mono-oleate or polyethoxylated castor oil), buffers for stabilizing the solution (e.g. citrates, acetates and phosphates) and/or antioxidants (e.g. ascorbic acid or sodium bisulfite).

For instance, a typical formulation for parenteral administration may contain from 5 to 50 mg of a compound of the invention for ml of final preparation. The compound will generally be formulated in water for injection, optionally in admixture with 10–20% of a surface-active agent which may be a polyoxyethylene sorbitan fatty acid ester, a polyoxyethylene castor oil derivative or a polyoxyethylene hydrogenated castor oil derivative and 0–20%; optionally, the formulation may further contain 10–20% of a solubilizing agent such as propylene glycol, dimethylacetamide, dimethylformamide, ter-butyl-N-hydroxycarmabate, 1,2-, 1,3-, or 1,4-butandiol, ethyl oleate, tetrahydrofurfurylpolyethylene-glycol 200, dimethyl isosorbide, benzyl alcohol and the like. A preferred solubilizing agent is propylene glycol.

Polyoxyethylene sorbitan fatty acid esters are commercially available and some of them are traded under the trade name "Tween". They are also known with the non-proprietary name of "polysorbates". Examples of them are polysorbate 20, 21, 40, 60, 61, 65, 80, 81 and 85. Preferred for use in the formulations of the invention is polysorbate 80 (sorbitan mono-9-octadecenoate, poly(oxy-1,2-ethanediyl) derivatives).

Polyoxyethylene castor oils and polyoxyethylene hydrogenated castor oils are also commercially available. Some of them are traded with the trade name "Cremophor". Examples of such compounds are those known as Cremophor EL (polyethoxylated castor oil), Cremophor RH 40 (polyethoxylated hydrogenated castor oil), Cremophor RH 60 (PEG 60 hydrogenated castor oil) or Emulphor EL-719 (polyoxyethylated vegetable oil).

If necessary, the pH of the preparation may be adjusted with a suitable buffering agent; conveniently, TRIS (i.e.trihydroxymethylaminomethane), phosphate or acetate buffers can be used.

A particularly preferred formulation for parenteral administration is one containing the compound of the invention in the salified form dissolved in distilled water, without any excipients.

An example of such a preparation is the following

| Compound 35 | 50 mg |
|---|---|
| Water for injection | 1 ml |
| pH 5 with acetic acid | |

Care should be taken to set the pH at a value of about 5 for helping the solubilization of the product, but not lower than 4.5 because possible hydrolysis of the oxazoline ring of the molecule may occur.

Examples of formulations of the compounds of the invention in admixture with suitable excipients, for parenteral administration, are the following:

| A) | compound 3s | 100 mg |
|---|---|---|
| | propylene glycol | 1 ml |
| | water for injection q.s. | 5 ml |
| | phosphate buffer pH 8–8.5 | |
| B) | compound 3s | 50 mg |
| | Cremophor RH 40 | 1 g |
| | water for injection q.s. | 10 ml |
| | phosphate buffer pH 8–8.5 | |

A further pharmaceutical formulation is represented by a formulation suitable for a topical application on an intact or damaged skin or mucous membrane. Examples of such formulations are powders, ointments, creams and lotions. The excipients in these formulations are the usual pharmaceutically acceptable vehicles such oleaginous ointment bases (e.g. cetyl esters wax, oleic acid, olive oil, paraffin, spermaceti, starch glycerite); absorbent ointment bases (e.g. anhydrous lanolin, hydrophylic petrolatum), emulsion ointment bases (e.g. cetyl alcohol, glyceryl monostearate, lanolin, stearic acid), water-soluble ointment bases (e.g. glycol ethers and their derivatives which include polyethylene glycols, poly(oxy-1,2-ethan ediyl)-alpha-hydro-omega-hydroxy-octadecanoate, polysorbates, and polyethylene glycols mono-stearates).

These formulations may contain other known excipients, such as preservatives and are prepared as known in the art and reported in reference handbooks such as Remington's Pharmaceutical Sciences, Seventeenth edition, 1985, Mack Publishing Co.

A preferred topic preparation is an ointment containing from 1% to 10% of a compound of the present invention.

Besides their use as medicaments in human and veterinary therapy, the compounds of the invention can also be used as animal growth promoters.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and CO., S. Francisco, USA, 1969 or "Livestock Feeds and Feeding" O and B books, Corvallis, Oreg., USA, 1977).

For better illustrating the invention, the following examples are given.

EXAMPLES

METHOD A—Reaction of GE2270 factor $A_3$ (see preparation no. 3) with L-serinamide (see preparation no. 19) and subsequent cyclization

Example A1

Preparation of Compound 3s

To a solution of GE2270 factor A3 (1 mmol) in DMF (10 ml) and TEA (2.2 mmol), DPPA (1.2 mmol) is added with stirring at 0° C. The temperature is allowed to rise to room temperature and after 4.5 h a solution of the hydrochloric salt of the selected L-serinamide prepared according to preparation 19 (1.2 mmol) and TEA (3 mmol) in DMF (3 ml) is added with stirring. The reaction is allowed to stir overnight at room temperature and then poured in aqueous 0.06 M NaHCO$_3$ (200 ml). The precipitate is collected by filtration, allowed to dry in the air and then purified by flash chromatography on silica gel 60 (400–230 mesh) using CH$_2$Cl$_2$ containing from 4% to 10% MeOH as the eluant. For facilitating elution, TEA from 0.1% to 1% (v/v) can be added to the eluant. Fractions containing the condensation product are combined and the solvent evaporated. Thorough washing of the obtained solid with ethyl ether yields the condensation product as a fine powder.

A solution of methoxycarbonylsulfamoyltriethylammonium hydroxide, inner salt (Burgess reagent) (5 mmol) in dry CH$_2$Cl$_2$ (3 ml) is added dropwise in an argon atmosphere at room temperature over 6 h to a stirred solution of the above condensation product (1 mmol) in dry tetrahydrofuran (THF) (30 ml). At the end of the addition of the Burgess reagent, the disappearance of the condensation product and the formation of a more hydrophilic adduct is controlled by HPLC; then, isopropanol (30 ml) is added to quench the excess of reagent. Stirring is continued for 2 h at room temperature and then the reaction mixture is refluxed (at about 70° C.) for 6 h to cyclize the oxazoline ring. After evaporation of the solvent under reduced pressure, the crude reaction mixture is purified on neutral aluminum oxide grade I (Merck) using from 2.5% to 5% MeOH in CH$_2$Cl$_2$ as the eluant. Fractions containing the title compound are combined and the solvent evaporated to dryness under reduced pressure to yield a solid which is further purified by flash chromatography on silica gel 60 (400–230 mesh) using CH$_2$Cl$_2$ containing from 4% to 10% MeOH as the eluant. For facilitating elution, TEA from 0.1% to 1% (v/v) can be added to the eluant. Fractions containing the title compound are combined and the solvent evaporated. Thorough washing of the solid with ethyl ether yields the title compound as a fine powder.

METHOD B—Reaction of starting material GE III (see preparation no. 6) with L-serinamide (see preparation No. 19)

Example B1

Preparation of Compound 3s

To a solution of starting material GEIII (1 mmol) in absolute ethanol (35 ml), CH$_2$Cl$_2$ (3–5 ml) and TEA (3 mmol), L-serinamide prepared according to preparation 19 (3 mmol) is added with stirring at room temperature. After about 30 h, the reaction mixture is poured in aqueous 0.06 M NaHCO$_3$ (100 ml) and the solid formed is isolated by centrifugation, washed with more water and then taken up in CH$_2$Cl$_2$ containing few drops of methanol. The solution is dried over Na$_2$SO$_4$ and the solvent evaporated under reduced pressure to yield a solid which is chromatographed on neutral aluminum oxide grade I (Merck) using from 2.5% to 5% MeOH in CH$_2$Cl$_2$ as eluant. Fractions containing the title compound are combined and the solvent is evaporated to dryness under reduced pressure to yield a solid which is further purified by flash chromatography on silica gel 60 (400–230 mesh) using CH$_2$Cl$_2$ containing from 4% to 10% MeOH as eluant. For facilitating elution, TEA from 0.1% to 1% (v/v) can be added to the eluant. Fractions containing the title compound are combined and the solvent evaporated. Thorough washing of the obtained solid with ethyl ether yields the title compound as a fine powder.

METHOD C—Reaction of starting material GE VII (see preparation no. 10) with the selected amine

Example C1

Preparation of Compound 3 (Epimers Mixture)

To a stirred solution of the sodium salt of compound GE VII (1 mmol) in DMF (30 ml), TEA (4 mmol) and aqueous 1N HCl (2 mmol) are added at room temperature. After a couple of minutes, the selected amine (1.5 mmol) and DPPA (1.2 mmol) are added thereto and stirring is continued overnight. The reaction mixture is then poured into water (150 ml) and the solid which forms is isolated by centrifugation, washed with water and then taken up in CH$_2$Cl$_2$ containing a few drops of methanol. The solution is dried over Na$_2$SO$_4$ and the solvent evaporated under reduced pressure to yield a solid which is chromatographed on neutral aluminum oxide grade I (Merck) using from 2.5% to 5% MeOH in CH$_2$Cl$_2$ as the eluant. Fractions containing the title compound are combined and the solvent evaporated. Thorough washing of the obtained solid with ethyl ether yields the title compound as a fine powder.

Example C2

Preparation of Compounds 1 to 19 (Epimers Mixture)

To a stirred solution of the sodium salt of compound GE VII (0.1 mmol) in DMF (9.7 ml), TEA (0.4 mmol) and aqueous 1N HCl (0.2 mmol) are added at room temperature. After a couple of minutes, a 0.2 M DMF* solution of the selected amine (0.2 mmol) and a 0.12 M DMF solution of DPPA (0.14 mmol) are added at the same temperature and stirring is continued overnight.

* If salts (hydrochloride, p-toluensulfonate, trifluoroacetate, etc) of the selected amine are used, 0.2 mmol of the salt of the selected amine is first dissolved in water (0.1 ml), then enough TEA to free the base is added and the volume is finally brought to 1 ml with DMF.

The compounds obtained according to the above examples have been characterized by their HPLC retention times, according to the following methodology:

| A | Column: RP18 (Merck) 5 μm |
|---|---|
| Eluent: | Phase A: ammonium formlate 0.05 M; |
|  | Phase B: acetonitrile |
| Gradient: | minutes 0 2 15 25 |
|  | % B 40 40 80 80 |
|  | from 2 to 15 minutes: linear gradient of B in A |
| Flow rate: | 0.7 ml/mm |
| Detection: | UV at 254 nm and 310 nm. |

| Compound | Retention time | Compound | Retention time |
|---|---|---|---|
| 1 | 13.0; 13,9 | 11 | 13.2; 14.4 |
| 2 | 12.6; 13.4 | 12 | 11.1; 11.4 |
| 3 | 12.5; 13.5 | 13 | 10.9 |
| 3s | 12.5 | 14 | 10.5; 10.9 |
| 4 | 12.5 | 15 | 13.9 |
| 5 | 12.7; 12.4 | 16 | 12.0 |
| 6 | 12.5; 12.7 | 17 | 12.4; 13.2 |
| 7 | 11.5; 11.9 | 18 | 9.6; 9.9 |
| 8 | 13.4 | 19 | 10.9 |
| 9 | 14.0; 14.5 | 20 | 14.5; 15.1 |
| 10 | 11.9 |  |  |

Compounds 3 and 3s have also been characterized by means of $^1$H-NMR spectra, FAB-MS spectra and UV spectra; methodologies and data are reported hereinafter.

The $^1$H-NMR spectra were recorded with a Bruker AM500 or AMX 600 spectrometer using DMSO-d$_6$ (hexadeuterodimethylsulfoxide) as solvent (s=singlet, br=broad singlet, d=doublet, dd=doublet of doublets, t=triplet, m=multiplet).

Compound 3

$^1$H-N.M.R. (DMSOd$_6$) δ(ppm): 0.84(d, 3H); 0.87(d, 3H); 0.95(br, 6H); 1.35(dd, 1H); 2.25–1.85(m, 5H); 2.47(d, 3H); 2.58(s, 3H); 2.65–2.30(m, 4H); 2.70(dd, 1H); 3.38(s, 3H); 3.55–3.00(m, 4H); 3.80(m, 2H); 3.98(dd, 1H); 4.28(m, 2H); 4.57(dd, 1H); 4.79(dd, 1H), 4.97(s, 2H); 5.00(dd, 1H); 5.20(dd, 1H); 5.25(m, 2H); 5.30(dd, 1H); 6.00(d, 1H); 7.40–7.20(m, 7H); 7.75(br, 1H); 8.27(m, 2H); 8.41(m, 2H); 8.53(s, 1H); 8.59(s, 1H); 8.65(m, 2H); 8.98(d, 1H).

Compound 3s $^1$H-N.M.R. (DMSOd$_6$) δ(ppm): 0.85(d, 3H); 0.87(d, 3H); 0.92(br, 6H); 1.35(dd, 1H); 2.20–1.86(m, 5H); 2.47(d, 3H); 2.58(s, 3H); 2.63–2.32(m, 4H); 2.71(dd, 1H); 3.38(s, 3H); 3.52–3.04(m, 4H); 3.79(m, 2H); 4.00(dd, 1H); 4.28(m, 2H); 4.57(dd, 1H); 4.81(dd, 1H); 4.95(s, 2H); 5.03(dd, 1H); 5.20(dd, 1H); 5.25(m, 2H); 5.30(dd, 1H); 6.01(d, 1H); 7.40–7.20(m, 7H); 7.77(br, 1H); 8.27(m, 2H); 8.40(m, 2H); 8.55(s, 1H); 8.57(s, 1H); 8.65(m, 2H); 8.96(d, 1H).

The FAB-MS spectra were obtained with a triple stage quadrupole spectrometer TSQ 700 Finningan.

Compound 3 FAB-MS m/z 1389 (MH$^+$, 100%);

Compound 3s FAB-MS m/z 1389 (MH$^+$, 100%).

The UV absorption spectra were recorded with a Perkin-Elmer spectrophotometer Mod. Lamda 16 (200–800 nm).

Compound 3 UV(MeOH) $\lambda_{max}$=310 (E1%, 1 cm.=247.2);

Compound 3s UV(MeOH) $\lambda_{max}$=310 (E1%, 1 cm.=245.6).

PREPARATION OF STARTING MATERIALS

REPARATION OF ANTIBIOTIC GE2270 STARTING MATERIALS

Preparation 1: GE2270 Factor A

GE2270 factor A is prepared by fermentation of *Planobispora rosea* ATCC 53773, as described in U.S. Pat. No. 5,202,241. Recovery and isolation of the factor are as described therein.

Preparation 2: GE2270 Factor A$_2$

4'-de[4-[[2-(aminocarbonyl)-1-pyrrolidinyl]carbonyl]-4,5-dihydro-2-oxazolyl]4'-[[(octahydro-1,4-dioxopyrrolo-[1,2-a]pyrazin-3-yl)methoxy]carbonyl] GE2270 factor A GE2270 factor A$_2$ is prepared by controlled acid hydrolysis from GE2270 factor A, as described in U.S. Pat. No. 5,139,778.

Preparation 3: GE2270 Factor A$_3$

4'-carboxy-4'-de[4-[[2-(aminocarbonyl)-1-pyrrolidinyl]-carbonyl]-4,5-dihydro-2-oxazolyl] GE2270 factor A GE2270 factor A$_3$ is prepared by controlled basic hydrolysis from GE2270 factor A$_2$, as described in U.S. Pat. No. 5,139,778.

Preparation 4: Starting Material GE I

4'-(aminocarbonyl)-4'-de[4-[[2-(aminocarbonyl)-1-pyrrolidinyl]carbonyl]-4,5-dihydro-2-oxazolyl] GE2270 factor A Antibiotic GE 2270 factor A$_2$ (1 mmol) is dissolved in a saturated solution of NH$_3$ in methanol (10 ml). The solution is allowed to stand for 3 days at room temperature and then is evaporated under reduced pressure. The residue is taken up in methanol (2 ml) and the title compound precipitated with water, filtered and allowed to dry in air. Thorough washing with ethyl ether yields the title compound (GE I) as a white powder.

Preparation 5: Starting Material GE II

4'-cyano-4'-de[4-[[2-(aminocarbonyl)-1-pyrrolidinyl]-carbonyl]-4,5-dihydro-2-oxazolyl] GE2270 factor A A solution of Burgess reagent (3.5 mmol) in dry CH$_2$Cl$_2$ (5 ml) is added dropwise over 30 min under an argon atmosphere to a well stirred solution of compound GE I (1 mmol) in dry CH$_2$Cl$_2$ (15 ml), dry THF (20 ml) and TEA (2.25 ml) at room temperature. After 16 h more Burgess reagent (1 mmol) is added in small portions and stirring is continued at room temperature for further 24 h. The reaction mixture is then evaporated to dryness under reduced pressure and the crude solid is purified by flash chromatography on silica gel 60 (400–230 mesh) using CH$_2$Cl$_2$/MeOH 95:5 as eluant. The title compound is obtained as a white powder.

Preparation 6: Starting Material GE III

4'-de[4-[[2-(aminocarbonyl)-1-pyrrolidinyl]carbonyl]-4,5-dihydro-2-oxazolyl]-4'-(ethoxyiminomethyl) GE2270 factor A Compound GE II (1 mmol) is dissolved in absolute ethanol (80 ml) and CHCl$_3$ (8 ml). The solution is cooled to 0° C. and dry HCl is bubbled through it for 6 h. The reaction mixture is then allowed to stand overnight at 4° C. and the solvent is evaporated under reduced pressure to a small volume. The concentrated solution is then carefully poured in an aqueous saturated solution of Na$_2$CO$_3$ and the resulting precipitate is centrifuged, washed twice with water and then redissolved in chloroform containing the minimum amount of ethanol to help solubilizing the product. The resulting solution is then transferred into a separatory funnel to remove the aqueous layer. The organic phase is dried over Na$_2$SO$_4$ and the solvent evaporated under reduced pressure to yield a white solid which is triturated with ether and filtered. The title compound is obtained as a white powder.

Preparation 7: Starting Material GE IV

9'-de[[2-(aminocarbonyl)-1-pyrrolidinyl]carbonyl]-9'-(methoxycarbonyl) GE2270 factor A To a solution of compound GE III (1 mmol) in a mixture of absolute ethanol (35 ml) and CH$_2$Cl$_2$ (3.5 ml), L-serine methyl ester hydrochloride (1.5 mmol) is added with stirring at room temperature under an argon atmosphere. After 4 days the solvent is evaporated under reduced pressure and the resulting crude is purified by flash chromatography on silica gel 60 (400–230 mesh) using CH$_2$Cl$_2$/MeOH 95:5 as eluant. The title compound is obtained as a white powder.

Preparation 8: Starting Material GE V

4'-(R,S)-carboxy-4'-de[[2-(aminocarbonyl)-1-pyrrolidinyl]-carbonyl] GE2270 factor A To a solution of compound GE IV (1 mmol) in dioxane (35 ml), 1N NaOH (2 mmol) is added at room temperature with stirring. After 15 min ethyl ether is added to precipitate the title compound which is collected by filtration. The sodium salt of title compound is obtained as white powder.

Preparation 9: Starting Material GE VI

9'-(R,S)-13'-de-(aminocarbonyl)-13'-(methoxycarbonyl) GE2270 factor A

To a solution of the sodium salt of compound GE V of (1 mmol) in DMF (25 ml), TEA (4 mmol), aqueous 1N HCl (0.5 ml), L-proline methyl ester (1.5 mmol) and DPPA (1.7 mmol) are added in the order with stirring at room temperature. After an overnight stirring, the reaction mixture is poured in water (80 ml) and the precipitate collected by filtration. The solid is taken up in a small volume of $CH_2Cl_2$ containing a few drops of MeOH to help the solubilization of the solid, dried over $Na_2SO_4$ and the solvent evaporated to dryness under reduced pressure. Flash chromatography on silica gel 60 (400–230 mesh) using $CH_2Cl_2$/MeOH 95:5 as eluant afforded the title compound as a white powder.

Preparation 10: Starting Material GE VII

9'-(R,S)-13'-carboxy-13'-de(aminocarbonyl) GE2270 factor A

To a solution of compound GE VI (1 mmol) in dioxane (30 ml), 1N NaOH (2.3 mmol) is added at room temperature with stirring. After 4 h ethyl ether is added to precipitate the title compound which is collected by filtration. The sodium salt of the title compounds obtained as a pale yellow powder.

PREPARATION OF THE AMINES STARTING MATERIALS

In the following, it is described the preparation of particular amines employed as starting materials for preparing the compounds of the inventions, which amines are not commercially available.

Preparation 11: Amine for Compound 13

A solution of N-Cbz-sarcosine (Novabiochem) (2.0 g, 8.96 mmol), N,N,N'-trimethyl-ethylenediamine (Aldrich) (1.25 ml, 9.86 mmol) and triethylamine (1.40 ml, 9.86 mmol) in dry DMF (30 ml) is stirred at room temperature. DPPA (2.2 ml, 9.86 mmol) is added and stirring at room temperature is continued for 2 hours. The reaction mixture is poured into water (500 ml), the pH is adjusted to 11 by addition of 1N NaOH and the aqueous phase is extracted with ethyl ether (3×200 ml). The organic phase is dried ($MgSO_4$) and concentrated to dryness. The crude product is purified by flash chromatography on silica gel 60 (400–230 mesh) with methylene chloride/methanol 8/2 to produce pure N,N,N'-trimethylethylenediamine N-Cbz-sarcosinamide as an oil.

A suspension of the above prepared N,N,N'-trimethylethylenediamine N-Cbz-sarcosinamide (2.0 g, 6.51 mmol) and 10% palladium on charcoal (200 mg) in methanol (40 ml) is hydrogenated at room temperature and under atmospheric pressure for 1 hour. The catalyst is then removed by filtration and concentration of the solvent produced the pure unprotected N,N,N'-trimethylethylenediamine sarcosinamide as an oil.

Preparation 12: Amine for Compound 14

A solution of N-Boc-L-alanine N-hydroxy-succinimide ester (Novabiochem) (2.0 g, 7 mmol) and N,N,N'-trimethylethylenediamine (Aldrich) (1.0 ml, 7.7 mmol) in dry DMF (30 ml) is stirred at room temperature overnight and then poured into water (600 ml), the pH is adjusted to 9 with sodium carbonate and the aqueous phase is extracted with ethyl ether (2×400 ml). The organic phase is dried ($MgSO_4$) and the solvent is evaporated in vacuo to yield N,N,N'-trimethyl-ethylenediamine N-Boc-L-alaninamide as a colourless oil.

The above prepared N,N,N'-trimethylethylenediamine N-Boc-L-alaninamide (1.7 g, 6.23 mmol) is dissolved at 0° C. in anhydrous TFA (10 ml), then stirred for 5 minutes. After concentration of the solvent at low temperature in vacuo and various washings of the oily product with ethyl ether, the crude trifluoroacetate salt is dissolved in water (10 ml), the pH of the aqueous solution is adjusted to 11 with 1N NaOH and then the product is extracted with $CH_2Cl_2$ (2×20 ml). The organic phase is dried ($MgSO_4$) and concentrated to dryness in vacuo to give pure N,N,N'-trimethylethylenediamine L-alaninamide trifluoroacetic salt as a gummy oil.

Preparation 13: Amine for Compound 15

A solution of N,N,N'-trimethylethylenediamine-sarcosinamide (see preparation 11) (750 mg, 4.33 mmol) in dry THF (15 ml) is stirred under argon at room temperature. Lithium aluminum hydride (495 mg, 13 mmol) is added in one portion, the temperature is brought to reflux and reflux is continued for additional 6 hours. After cooling to 0° C. ethyl acetate (1.5 ml) and 2.5M NaOH (6 ml, 1.2 equivalents) are carefully added followed by solid $MgSO_4$. The suspension is stirred at room temperature for 15 minutes and then filtered. After concentration of the solvent pure N-(2-dimethylaminoethyl)-N-(2-methylaminoethyl)-methylamine is obtained as an oil.

Preparation 14: Amine for Compound 16

1-Benzylpiperazine (Aldrich) (9 ml, 50 mmol) and potassium carbonate (14 g, 0.1 mole) are added at room temperature to a stirred solution of 3-dimethylaminopropyl chloride hydrochloride (Aldrich) (15.8 g, 0.1 mol) in absolute ethanol (300 ml). The reaction mixture is refluxed for 6 hours, the solvent is evaporated in vacuo and water (300 ml) is added to the resulting oil. After extraction with $CH_2Cl_2$ (200 ml), the organic phase is washed with water (200 ml), dried ($MgSO_4$) and the solvent is evaporated in vacuo to yield the 1-benzyl-4-substituted piperazine as an oil.

A suspension of the above prepared 1-benzyl-4-substituted piperazine (9.0 g, 35 mmol) and 10% palladium on charcoal (3 g) in 95% ethanol (300 ml) is hydrogenated at room temperature and under atmospheric pressure for 6 hours. The catalyst is filtered off and the solution is concentrated to dryness under reduced pressure to yield the debenzylated product as an oil.

Preparation 15: Amine for Compound 17

The reaction is carried out as reported in preparation 11 by condensing N-Cbz-sarcosine (Novabiochem) (2.0 g, 8.96 mmol) with 1-methylpiperazine (Aldrich) (986 mg, 9.86 mmol) and then removing the Cbz-protecting group to yield the expected compound as an oil that is then reduced with lithium aluminum hydride as described in preparation 13 to yield the expected triamine as an oil.

Preparation 16: Amine for Compound 18

The reaction is carried out as reported in preparation 11 by condensing N-Cbz-sarcosine (Novabiochem) (2.0 g, 8.96 mmol) with N-(2-hydroxyethyl)piperazine (Aldrich) (1.28 g, 9.86 mmol) and then removing the Cbz-protecting group to yield the expected compound as an oil that is then reduced with lithium aluminium hydride as described in preparation 13 to yield the expected triaminealcohol as an oil.

Preparation 17: Amine for Compound 19

1-(4-morpholinocarbonylmethyl)-piperazine (Acros Chimica) (2.13 g, 10 mmol) is reduced as reported in preparation 13 to yield the expected triamine as an oil.

Preparation 18: Amine for Compound 20

To a solution of (S)-(−)-2-pyrrolidone-5-carboxylic acid (Aldrich) (500 mg, 3.87 mmol), N,N,N'- trimethylethylenediamine (Aldrich) (0.54 ml, 4.26 mmol) and triethylamine (0.60 ml, 4.26 mmol) in dry DMF (5 ml), DPPA (0.95 ml, 4.26 mmol) is added under stirring at room temperature. Stirring is continued for 1 hour, then the mixture is poured into ethyl ether (100 ml). The solid that precipitated is filtered, washed with additional ethyl ether (20 ml) and allowed to dry in air to yield the expected condensation product as a white solid.

Reduction of the above described compound (560 mg, 2.62 mmol) according to preparation 13 yielded the expected triamine as an oil.

PREPARATION OF THE SERINAMIDES STARTING MATERIALS

Preparation 19: Preparation of the L-serinamide Starting Material Employed in Examples A1 abd B1 for Preparing Compound 3s A mixture of Cbz-L-Proline (Novabiochem) (145.0 g, 0.58 mol) and N-hydroxysuccinimide (Aldrich) (66.9 g, 0.58 mol) in EtOAc (1.8 L) is cooled at −5° C. with stirring under $N_2$ atmosphere. To this solution, a solution of DCC (132.1 g, 0.64 mol) in EtOAc (265 ml) is added over 20 min so to mantain the internal temperature at −5° C. The temperature is then allowed to rise to ambient temperature and stirring is continued for additional 3 hours. Precipitated dicyclohexylurea is filtered off and the filtrate is used as such in the next step.

To the above prepared solution of N-Cbz-L-proline N-hydroxysuccinimide ester, N,N-diethyl-ethylenediamine (Aldrich) (67.6 g, 0.58 mol) is added over 15 min while stirring at room temperature. After 18 hours the solid that had formed is filtered off, washed over the filter with EtOAc (300 ml) and the filtrate is extracted with 1.04M HCl (725 ml). The aqueous extracts are cooled by an ice-bath, the pH is brought to 10 by careful addition of 1M NaOH and then extracted with $CH_2Cl_2$ (4×730 ml). The organic extracts are combined, dried ($MgSO_4$) and the solvent evaporated to dryness under reduced pressure to provide an oil which is diluted with $Et_2O$ (60 ml) and hexane (2 L) under stirring. After 18 hours at room temperature and 1 hour in an ice-bath, the solid product is filtered off, washed with an ice-cold 9:1 mixture of hexane/$Et_2O$ (2×200 ml) and air-dried at ambient temperature to yield N,N-diethylethylenediamine N-Cbz-L-prolinamide as a white powder.

10% Pd/C (5 g) is charged to a 1-L 3-necked flask fitted with a magnetic stirrer, thermometer and continuous $N_2$ purge. The catalyst is wetted with water (20 ml) and then ammonium formate (13.6 g, 0.22 mol) is added in one portion. The mixture is stirred while adding a solution of the above prepared N,N-diethylethylenediamine N-Cbz-L-prolinamide (50 g, 0.14 mol) in methanol (189 ml) over 20 min. After 30 min the reaction is completed, the catalyst is filtered off, washed over the filter with additional methanol (4×25 ml) and the filtrate is evaporated to dryness under reduced pressure to yield N,N-diethylethylenediamine-L-prolinamide as an oil.

A mixture of N-Cbz-L-serine (Novabiochem) (100 g, 0.42 mol) and pentafluorophenol (Aldrich) (84.7 g, 0.46 mol) in anhydrous DMF (250 ml) is cooled with stirring under $N_2$ to −10° C. To this solution, a solution of DCC (95.0 g, 0.46 mol) in anhydrous DMF (125 ml) is added over 30 min while keeping the reaction temperature at −10° C. The reaction mixture is stirred at −10° to −5° C. for an additional 30 min and then at room temperature for 3 hours. The reaction mixture is poured into water (3.76 L). After stirring for 15 min, the solid that precipitated out is filtered, washed over the filter with water (3×500 ml) and air dried at room temperature. The solid is then taken up in EtOAc (1 L) and the residual solid (mainly dicyclohexylurea) is filtered off and washed with more EtOAc (3×150 ml). The combined EtOAc solutions are evaporated to dryness under reduced pressure.

The residual solid is dissolved in hot $CH_2Cl_2$ (3.2 L). The hot solution is gravity filtered and the solvent is boiled off until solid began to crystallize. The solid which crystallized is filtered and air dried to ambient temperature to give N-Cbz-L-serine pentafluorophenyl ester as a white solid.

A solution of N,N-diethylethylenediamine-L-prolinamide (63.1 g, 0.30 mol) in $CH_2Cl_2$ (500 ml) is charged to 2-L 3-necked flask fitted with a magnetic stirrer, thermometer and continuous $N_2$ purge. The solution is stirred while adding N-Cbz-L-serine pentafluorophenyl ester (121.6 g, 0.30 mol) as a solid over 10 min. The reaction mixture is stirred for an additional 1 hour at room temperature and then is washed with 1N NaOH (105 ml followed by 2×210 ml). The organic phase is separated, dried ($MgSO_4$) and then evaporated to dryness under reduced pressure. The glassy product is diluted with $Et_2O$ (200 ml) and the mixture is warmed to 30° C. and solid began to form. After all of the glass had solified, the mixture is diluted with pentane (200 ml). Solid is filtered off, washed with pentane, then air-dried at room temperature to give a solid which is slurried in $Et_2O$ (250 ml). Solid is filtered off and allowed to air-dry at room temperature to give the expected N-Cbz-L-serinamide as a white powder.

Deprotection of the Cbz-protecting group is carried out just before usage of the serinamide.

A suspension of the above prepared N-Cbz-L-serinamide (5.0 g, 11.52 mmol) and 10% palladium on charcoal (500 mg) in methanol (90 ml) is hydrogenated at room temperature and atmospheric pressure in the presence of 20% methanolic HCl (4.6 ml) for 1 hour. The catalyst is filtered off, washed over the filter with methanol (2×100 ml) and the solvent evaporated to dryness under reduced pressure. Trituration of the waxy solid with $Et_2O$ yielded the expected serinamide hydrochloric salt as a white powder.

What is claimed is:

1. Basic amide compounds of GE 2270 and GE 2270-like antibodies of formula I

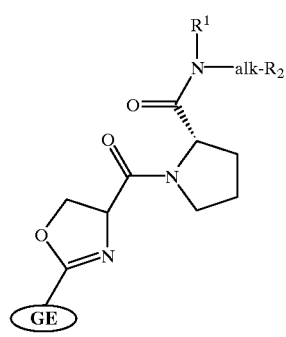

wherein:
  $R^1$ represents hydrogen, ($C_1$–$C_4$)alkyl or di($C_1$–$C_4$) alkylamino($C_1$–$C_4$)alkylene, alk represents ($C_1$–$C_4$) alkylene or ($C_2$–$C_5$)alkylene-carbonyl,
  $R^2$ represents a $NR^3R^4$ group wherein
  $R^3$ represents ($C_1$–$C_4$)alkyl, hydroxy($C_1$–$C_4$)alkylene, or di($C_1$–$C_4$)alkylamino-($C_1$–$C_4$)alkylene, and
  $R^4$ represents ($C_1$–$C_4$)alkyl, di($C_1$–$C_4$)alkylamino-($C_1$–$C_4$)alkylene or hydroxy($C_1$–$C_4$)alkylene,
  or a five or six membered heterocycle ring having one or two nitrogen atoms, or one nitrogen atom and one oxygen atom, with the remaining atoms of the heterocycle ring being carbon atoms or oxygen atoms, wherein any nitrogen atom or any carbon atom may be optionally substituted with a group selected from $(C_1-C_4)$alkyl, hydroxy$(C_1-C_4)$alkylene, di$(C_1-C_4)$alkylamino and di$(C_1-C_4)$alkylamino-$(C_1-C_4)$alkylene;

or $R^1$ and alk-$R^2$ together with the adjacent nitrogen atom form a five or six membered heterocycle ring having one or two nitrogen atoms or having one nitrogen atom and one oxygen atom, with the remaining atoms of the heterocycle ring being carbon atoms, wherein any nitrogen atom or any carbon atom may be optionally substituted with a group selected from $(C_1-C_4)$alkyl, di$(C_1-C_4)$alkylamino, di$(C_1-C_4)$alkylamino$(C_1-C_4)$ alkylene, hydroxy$(C_1-C_4)$alkylene and a alk$_2$-$R^5$ group wherein alk$_2$ is $(C_1-C_4)$alkylene and $R^5$ is a $NR^6R^7$ group wherein $R^6$ represents $(C_1-C_4)$alkyl or di$(C_1-C_4)$alkyl-amino $(C_1-C_4)$alkylene and $R^7$ represents $(C_1-C_4)$alkyl or di$(C_1-C_4)$alkyl-amino $(C_1-C_4)$alkylene or a five or six membered heterocycle ring having one or two nitrogen atoms, or one nitrogen atom and one oxygen atom, with the remaining atoms of the heterocycle ring being carbon atoms, wherein any nitrogen atom or any carbon atom may be optionally substituted with a group selected from $(C_1-C_4)$alkyl, hydroxy $(C_1-C_4)$alkylene, di$(C_1-C_4)$alkylamino and di$(C_1-C_4)$ alkylamino$(C_1-C_4)$alkylene and the group of formula

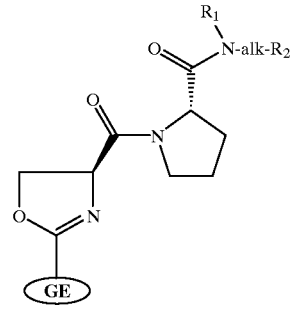

represents the antibiotic core portion of the formula

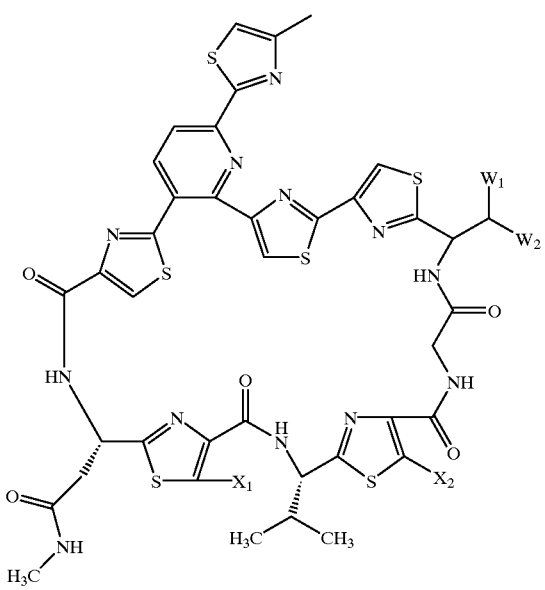

wherein:
$W^1$ represents phenyl
$W^2$ represents hydroxy or both $W^1$ and $W^2$ represent methyl, $X^1$ represents hydrogen or methyl, $X^2$ represents hydrogen, methyl or methoxymethylene, with the proviso that when both $W^1$ and $W^2$ are methyl, then $X^1$ is methyl and $X^2$ is hydrogen, or a pharmaceutical acceptable salt thereof.

2. Compound according to claim 1 of formula II wherein $R^1$, alk, $R^2$ and the group GE are as defined in claim 1.

3. Compound according to claim 1 wherein $R^1$ represents hydrogen or $(C_1-C_4)$alkyl, alk represents $(C_1-C_4)$alkylene or $(C_2-C_5)$alkylene-carbonyl, $R^2$ represents a $NR^3R^4$ group wherein $R^3$ represents $(C_1-C_4)$alkyl and $R^4$ represents $(C_1-C_4)$alkyl or di$(C_1-C_4)$alkylamino-$(C_1-C_4)$alkylene, or a five or six membered heterocycle ring having one or two nitrogen atoms, with the remaining atoms of the heterocycle ring being carbon atoms, wherein any nitrogen atom or any carbon atom maybe optionally substituted with a group selected from $(C_1-C_4)$alkyl and hydroxy$(C_1-C_4)$alkylene;

or $R^1$ and alk-$R^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_4)$alkyl, di$(C_1-C_4)$alkylamino, di$(C_1-C_4)$alkylamino$(C_1-C_4)$ alkylene and a alk$_2$-$R^5$ group wherein alk$_2$ is $(C_1-C_2)$alkylene and $R^5$ is a $NR^6R^7$ group wherein $R^6$ represents $(C_1-C_4)$alkyl and $R^7$ represents $(C_1-C_4)$alkyl or di$(C_1-C_4)$alkyl-amino $(C_1-C_4)$alkylene or a five or six membered heterocycle ring having one or two nitrogen atoms or one nitrogen atom and one oxygen atom, with the remaining atoms of the heterocycle ring being carbon atoms.

4. Compound according to claim 1 wherein $R^1$ represents hydrogen or $(C_1-C_2)$alkyl, alk represents $(C_1-C_3)$alkylene or $(C_2-C_3)$alkylene-carbonyl, $R^2$ represents a $NR^3R^4$ group wherein $R^3$ represents $(C_1-C_3)$alkyl and $R^4$ represents $(C_1-C_3)$alkyl or di$(C_1-C_2)$alkylamino-$(C_1-C_2)$alkylene, or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl and hydroxy$(C_1-C_2)$alkylene;

or $R^1$ and alk-$R^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl, di$(C_1-C_2)$alkylamino, di$(C_1-C_2)$alkylamino$(C_1-C_2)$ alkylene and a alk$_2$-$R^1$ group wherein alk$_2$ is $(C_1-C_2)$alkylene and $R^5$ is a NR$^6$R$^7$ group wherein $R^6$ represents $(C_1-C_2)$alkyl and $R^7$ represents $(C_1-C_2)$alkyl or di$(C_1-C_2)$alkyl-amino $(C_1-C_2)$alkylene or a five or six membered heterocycle ring having one or two nitrogen atoms or one nitrogen atom and one oxygen atom, with the remaining atoms of the heterocycle ring being carbon atoms.

5. Compound according to claim 1 wherein the group GE is such that $W^1$ is phenyl, $W^2$ is hydroxy, $X^1$ is methyl, $X^2$ is methoxymethylene and $R^1$ represents hydrogen or $(C_1-C_2)$alkyl, alk represents $(C_1-C_3)$alkylene, $R^2$ represents a NR$^3$R$^4$ group wherein $R^3$ represents $(C_1-C_3)$alkyl and $R^4$ represents $(C_1-C_3)$alkyl or di$(C_1-C_2$alkylamino-$(C_1-C_2)$alkylene, or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl and hydroxy$(C_1-C_2)$alkylene;

or $R^1$ and alk-$R^2$ together with the adjacent nitrogen atom form a five or six membered heterocycle ring having one or two nitrogen atoms with the remaining atoms of the heterocycle ring being carbon atoms, wherein any nitrogen atom or any carbon atom may be optionally substituted with a group selected from $(C_1-C_2)$alkyl, di$(C_1-C_2)$alkylamino, di$(C_1-C_2)$alkylamino$(C_1-C_2)$ alkylene and a alk$_2$-$R^5$ group wherein alk$_2$ is $(C_1-C_2)$alkylene and $R^5$ is a NR$^6$R$^7$ group wherein $R^6$ represents $(C_1-C_2)$alkyl and $R^7$ represents $(C_1-C_2)$alkyl or di$(C_1-C_2)$alkyl-amino $(C_1-C_2)$alkylene or a five or six membered heterocycle ring having one or two nitrogen atoms or one nitrogen atom and one oxygen atom, with the remaining atoms of the heterocycle ring being carbon atoms.

6. Compound according to claim 2 wherein $R^1$ represents hydrogen or $(C_1-C_4)$alkyl, alk represents $(C_1-C_4)$alkylene or $(C_2-C_5)$alkylene-carbonyl, $R^2$ represents a NR$^3$R$^4$ group wherein $R^3$ represents $(C_1-C_4)$alkyl and $R^4$ represents $(C_1-C_4)$alkyl or di$(C_1-C_4)$alkylamino-$(C_1-C_4)$alkylene, or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_4)$alkyl and hydroxy$(C_1-C_4)$alkylene;

or $R^1$ and alk-$R^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_4)$alkyl, di$(C_1-C_4)$alkylamino, di$((C_1-C_4)$alkylamino$(C_1-C_4)$ alkylene and a alk$_2$-$R^5$ group wherein alk$_2$ is $(C_1-C_4)$alkylene and $R^5$ is a NR$^6$R$^7$ group wherein $R^6$ represents $(C_1-C_4)$alkyl and $R^7$ represents $(C_1-C_4)$alkyl or di$(C_1-C_4)$alkyl-amino $(C_1-C_4)$alkylene or a five or six membered heterocycle ring having one or two nitrogen atoms or one nitrogen atom and one oxygen atom, with the remaining atoms of the heterocycle ring being carbon atoms.

7. Compound according to claim 2 wherein $R^1$ represents hydrogen or $(C_1-C_2)$alkyl, alk represents $(C_1-C_3)$alkylene or $(C_2-C_3)$alkylene-carbonyl, $R^2$ represents a NR$^3$R$^4$ group wherein $R^3$ represents $(C_1-C_3)$alkyl and $R^4$ represents $(C_1-C_3)$alkyl or di$(C_1-C_2)$alkylamino-$(C_1-C_2)$alkylene, or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl and hydroxy$(C_1-C_2)$alkylene;

or $R^1$ and alk-$R^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl, di$(C_1-C_2)$alkylamino, di$(C_1-C_2)$alkylamino$(C_1-C_2)$ alkylene and a alk$_2$-$R^5$ group wherein alk$_2$ is $(C_1-C_2)$alkylene and $R^5$ is a NR$^6$R$^7$ group wherein $R^6$ represents $(C_1-C_2)$alkyl and $R^7$ represents $(C_1-C_2)$alkyl or di$(C_1-C_2)$alkyl-amino $(C_1-C_2)$alkylene or a five or six membered heterocycle ring having one or two nitrogen atoms or one nitrogen atom and one oxygen atom, with the remaining atoms of the heterocycle ring being carbon atoms.

8. Compound according to claim 2 wherein the group GE is such that $W^1$ is phenyl, $W^2$ is hydroxy, $X^1$ is methyl, $X^2$ is methoxymethylene and $R^1$ represents hydrogen or $(C_1-C_2)$alkyl, alk represents $(C_1-C_3)$alkylene, $R^2$ represents a NR$^3$R$^4$ group wherein $R^3$ represents $(C_1-C_3)$alkyl and $R^4$ represents $(C_1-C_3)$alkyl or di$(C_1-C_2)$alkylamino-$(C_1-C_2)$alkylene, or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl and hydroxy$(C_1-C_2)$alkylene;

or $R^1$ and alk-$R^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl, di$(C_1-C_2)$alkylamino, di$(C_1-C_2)$alkylamino$(C_1-C_2)$alkylene and a alk$_2$-$R^5$ group wherein alk$_2$ is $(C_1-C_2)$alkylene and $R^5$ is a $NR^6R^7$ group wherein $R^6$ represents $(C_1-C_2)$alkyl and $R^7$ represents $(C_1-C_2)$alkyl or di$(C_1-C_2)$alkyl-amino$(C_1-C_2)$alkylene or a five or six membered heterocycle ring having one or two nitrogen atoms or one nitrogen atom and one oxygen atom, with the remaining atoms of the heterocycle ring being carbon atoms.

9. A compound according to claim 1 which is

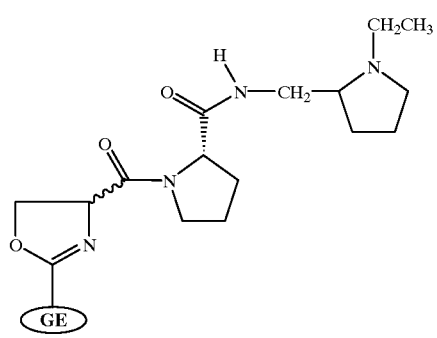

10. A compound according to claim 1 which is

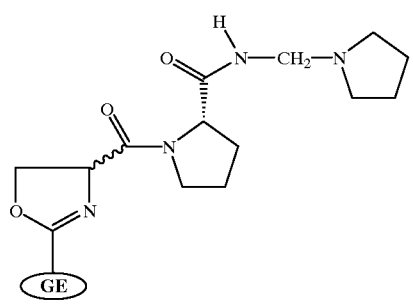

11. A compound according to claim 1 which is

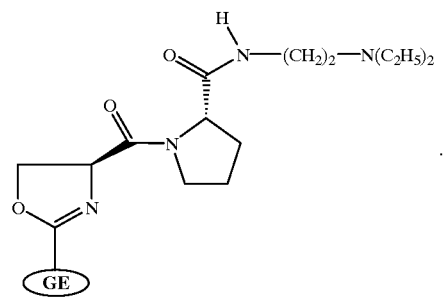

12. A compound according to claim 1 which is

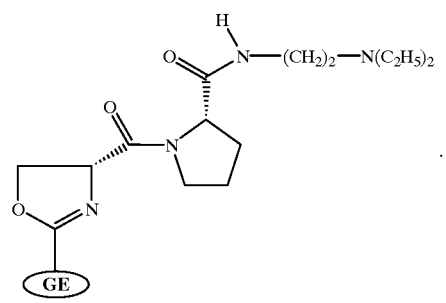

13. A compound according to claim 1 which is

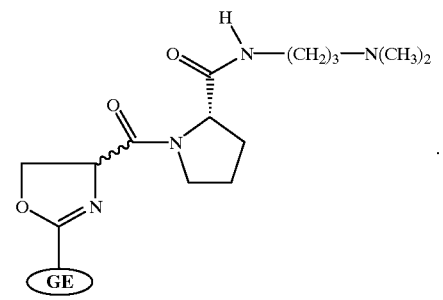

14. A compound according to claim 1 which is

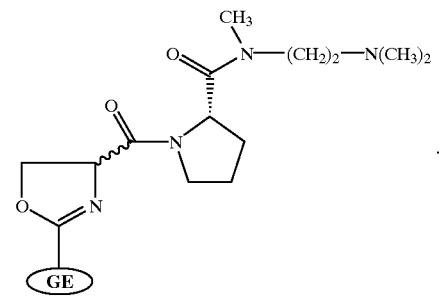

15. A compound according to claim 1 which is
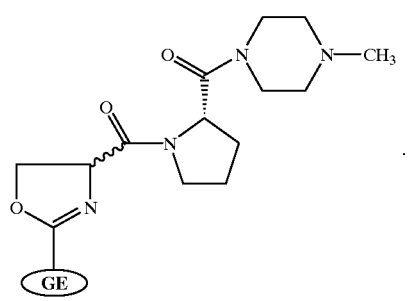
16. A compound according to claim 1 which is
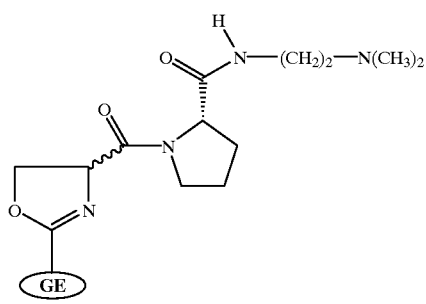
17. A compound according to claim 1 which is
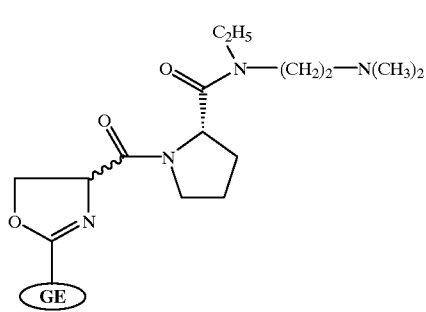
18. A compound according to claim 1 which is
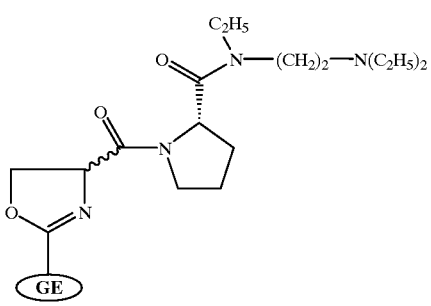
19. A compound according to claim 1 which is
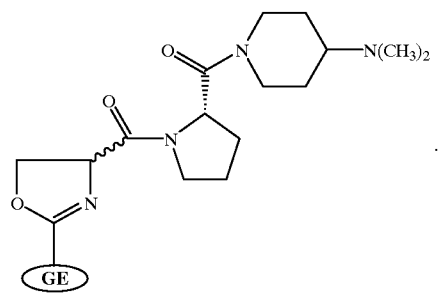
20. A compound according to claim 1 which is
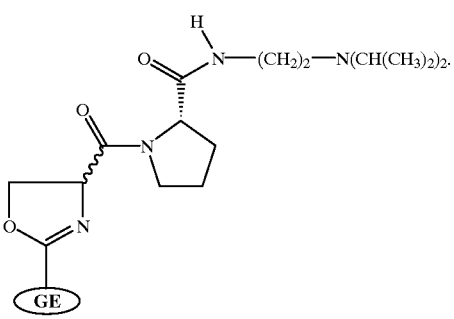
21. A compound according to claim 1 which is
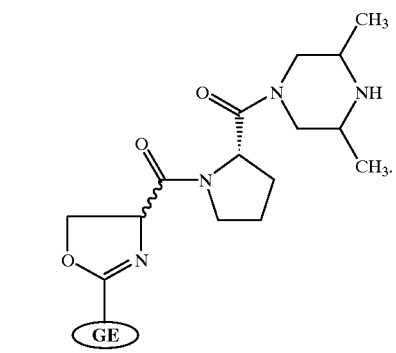
22. A compound according to claim 1 which is
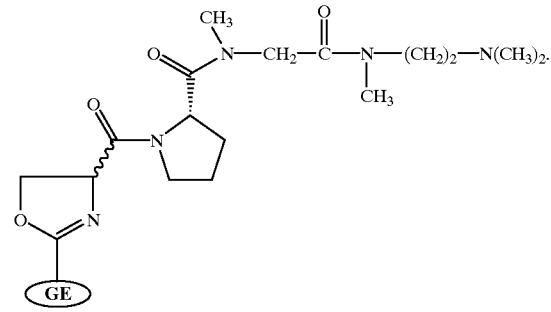

23. A compound according to claim 1 which is

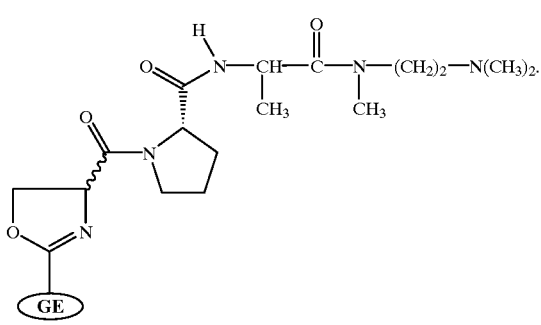

24. A compound according to claim 1 which is

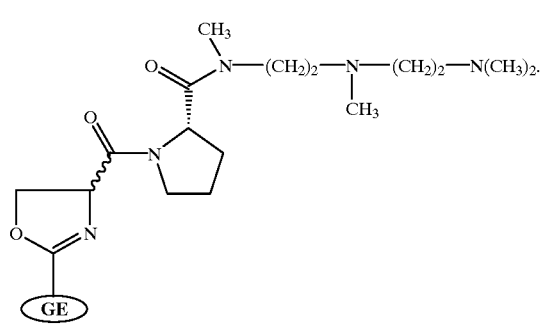

25. A compound according to claim 1 which is

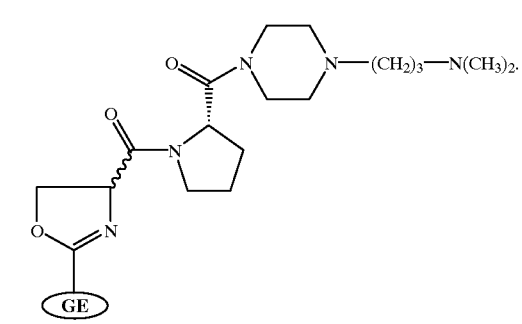

26. A compound according to claim 1 which is

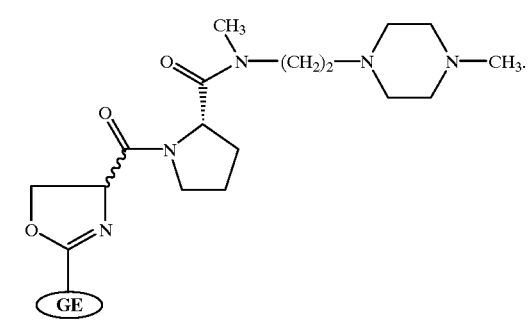

27. A compound according to claim 1 which is

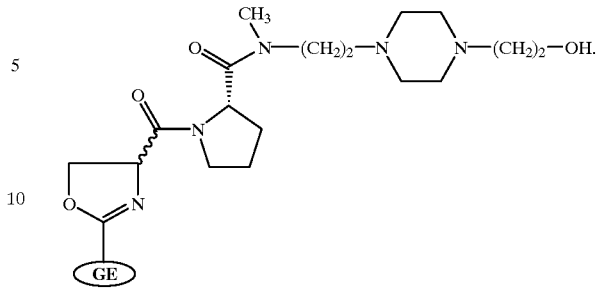

28. A compound according to claim 1 which is

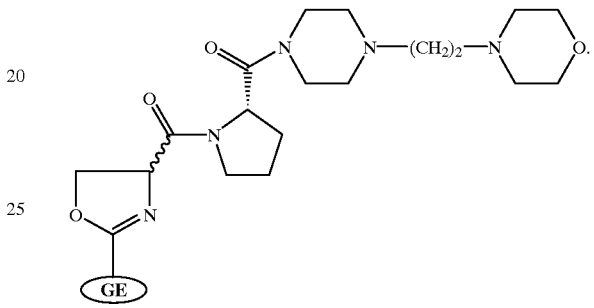

29. A compound according to claim 1 which is

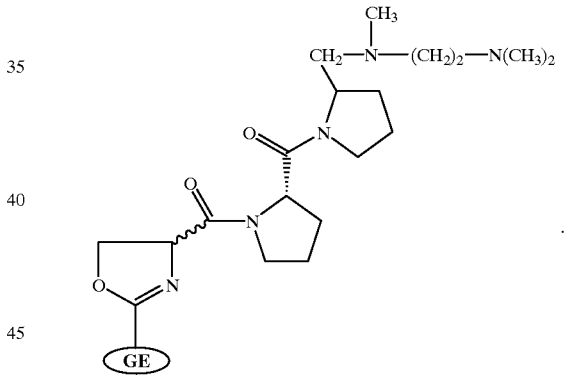

30. Compound of formula

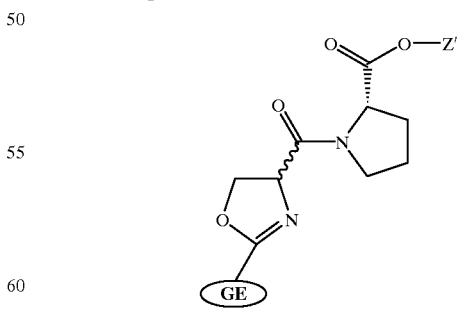

wherein Z' represents $(C_1-C_4)$alkyl and GE is as defined in claim 1.

31. Process for preparing a compound of claim 1 which comprises:

a) reacting a compound of formula III

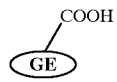
III wherein the group GE is as defined in formula I, with a serinamide, or an acid addition salt thereof, of formula IV:

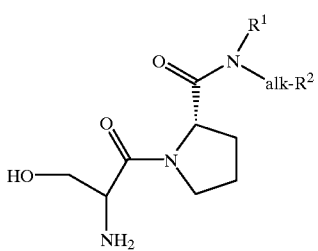
IV wherein $R^1$, alk and $R^2$ are as in claim 1, in an inert aprotic organic solvent in the presence of a condensing agent;

b) cyclizing the serine moiety of the obtained compound of formula IIIa

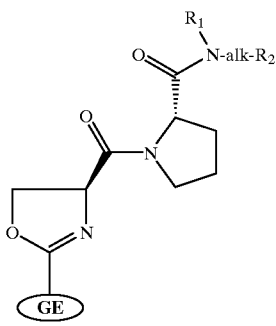
IIIa with a suitable cyclizing reactant, in order to obtain the desired compound of formula I.

32. Process for preparing a compound of claim 1 which comprises reacting a compound of formula V

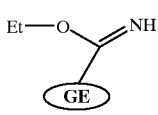
V wherein the group GE is as defined in claim 1, with a serinamide, or an acid addition salt thereof, of formula IV:

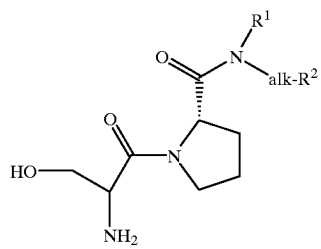
IV wherein $R^1$, alk and $R^2$ are as in claim 1, in a protic organic solvent.

33. Process for preparing a compound of claim 1 which comprises reacting a compound of formula VI

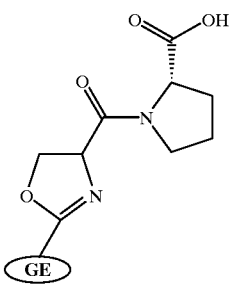
VI or a base addition salt thereof, wherein the group GE is as defined in formula I, with an amine, or an acid addition salt thereof, of formula IVa:

$$H-N\begin{matrix}R^1\\ alk-R^2\end{matrix}$$
IVa wherein $R^1$, alk, and $R^2$ are as defined in formula I, in the presence of an inert organic solvent and of a condensing agent.

34. Pharmaceutical composition containing a compound of claim 1 in admixture with a pharmaceutically acceptable carrier.

35. Pharmaceutical composition containing a compound of claim 2 in admixture with a pharmaceutically acceptable carrier.

36. Pharmaceutical composition containing a compound of claim 3 in admixture with a pharmaceutically acceptable carrier.

37. Pharmaceutical composition containing a compound of claim 4 in admixture with a pharmaceutically acceptable carrier.

38. Pharmaceutical composition containing a compound of claim 5 in admixture with a pharmaceutically acceptable carrier.

39. Method for the treatment of bacterial infections comprising administering an effective amount of a compound of claim 1 to a patient in need thereof.

40. Method for the treatment of bacterial infections comprising administering an effective amount of a compound of claim 2 to a patient in need thereof.

41. Method for the treatment of bacterial infections comprising administering an effective amount of a compound of claim 3 to a patient in need thereof.

42. Method for the treatment of bacterial infections comprising administering an effective amount of a compound of claim 4 to a patient in need thereof.

43. Method for the treatment of bacterial infections comprising administering an effective amount of a compound of claim 5 to a patient in need thereof.

* * * * *

UNITED STATES PATENT AND TRADEMARK OFFICE
CERTIFICATE OF CORRECTION

PATENT NO : 6,143,739
DATED : November 7, 2000
INVENTOR(S) : Sergio Lociuro et al.

It is certified that error appears in the above-identified patent and that said Letters Patent are hereby corrected as shown below:

Column 34, line 40 "antibodies" should be - - antibiotics - -.

Formula 1 "GE" shouldn't have a circle around it.

Column 37, line 12, "R1" should be - -R5 - - .

Column 38, line 14 "(C1 - C4)" should be - - (C1 - C2) - -.

Column 45, the second formula is wrong.

Column 46, line 34 "of formula" should be - - of general formula - -.

Signed and Sealed this

Twenty-ninth Day of May, 2001

Attest:

NICHOLAS P. GODICI

Attesting Officer    Acting Director of the United States Patent and Trademark Office